United States Patent
Stigall et al.

(10) Patent No.: US 10,709,312 B2
(45) Date of Patent: *Jul. 14, 2020

(54) TRANSITIONAL REGION HAVING CUTS AND A SKIVE FOR AN IMAGING CATHETER

(71) Applicant: Volcano Corporation, San Diego, CA (US)

(72) Inventors: Jeremy Stigall, Carlsbad, CA (US); Maritess Minas, San Diego, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/375,963

(22) Filed: Apr. 5, 2019

(65) Prior Publication Data

US 2019/0231170 A1    Aug. 1, 2019

Related U.S. Application Data

(63) Continuation of application No. 15/800,655, filed on Nov. 1, 2017, now Pat. No. 10,292,573, which is a
(Continued)

(51) Int. Cl.
*A61B 1/04* (2006.01)
*A61B 1/00* (2006.01)
(Continued)

(52) U.S. Cl.
CPC ........ *A61B 1/00078* (2013.01); *A61B 1/3137* (2013.01); *A61B 5/0066* (2013.01);
(Continued)

(58) Field of Classification Search
CPC . A61B 1/00078; A61B 1/3137; A61B 5/0066; A61B 5/0084; A61B 8/12;
(Continued)

(56) References Cited

U.S. PATENT DOCUMENTS

| | | | |
|---|---|---|---|
| 4,841,977 A | 6/1989 | Griffith et al. |
| 5,125,137 A | 6/1992 | Corl et al. |
| 6,066,114 A | 5/2000 | Goodin et al. |
| 6,078,831 A | 6/2000 | Belef |
| 6,078,931 A | 6/2000 | Motoyama |

(Continued)

FOREIGN PATENT DOCUMENTS

EP    0419277 B1    3/1991

OTHER PUBLICATIONS

International Searching Authority/European Patent Office, "Communication—Extended European Search Report," for European Application No. 13866063.4, dated Jul. 7, 2016, 7 pages.
(Continued)

*Primary Examiner* — Matthew J Kasztejna

(57) ABSTRACT

An imaging device for imaging a portion of a patient's vasculature with an imaging element may include a proximal portion having a relatively higher stiffness that provides rigidity for pushing the imaging device through a patient's vasculature, and may include a distal portion having a relatively lower stiffness that enables threading through a curved vasculature of the patient. The imaging device also may include a transition region disposed between the proximal portion and the distal portion.

17 Claims, 8 Drawing Sheets

Related U.S. Application Data continuation of application No. 14/103,532, filed on Dec. 11, 2013, now Pat. No. 9,833,125.

(60) Provisional application No. 61/738,710, filed on Dec. 18, 2012, provisional application No. 61/738,831, filed on Dec. 18, 2012, provisional application No. 61/738,864, filed on Dec. 18, 2012, provisional application No. 61/738,896, filed on Dec. 18, 2012.

(51) Int. Cl.
| | | |
|---|---|---|
| *A61B 1/313* | (2006.01) | |
| *A61B 8/12* | (2006.01) | |
| *A61B 5/00* | (2006.01) | |
| *A61B 8/00* | (2006.01) | |
| *A61M 25/00* | (2006.01) | |

(52) U.S. Cl.
CPC .............. *A61B 5/0084* (2013.01); *A61B 8/12* (2013.01); *A61B 8/445* (2013.01); *A61B 8/4461* (2013.01); *A61M 25/005* (2013.01); *A61M 25/0052* (2013.01); *A61M 25/0053* (2013.01)

(58) Field of Classification Search
CPC .... A61B 8/445; A61B 8/4461; A61M 25/005; A61M 25/0052; A61M 25/0053
USPC ........ 600/109, 139–143, 459, 462, 466–467, 600/478
See application file for complete search history.

(56) References Cited

U.S. PATENT DOCUMENTS

| | | |
|---|---|---|
| 6,102,890 A | 8/2000 | Stivland et al. |
| 6,107,004 A | 8/2000 | Donadio, III |
| 6,575,958 B1 | 6/2003 | Happ et al. |
| 7,294,124 B2 | 11/2007 | Eidenschink |
| 8,512,282 B2 | 8/2013 | Grovender et al. |
| 2003/0093059 A1 | 5/2003 | Griffin et al. |
| 2004/0092868 A1 | 5/2004 | Murray, III |
| 2005/0215942 A1 | 9/2005 | Abrahamson et al. |
| 2006/0074318 A1 | 4/2006 | Ahmed et al. |
| 2006/0142696 A1 | 6/2006 | Kumoyama et al. |
| 2007/0066900 A1 | 3/2007 | O'Keeffe |
| 2010/0168669 A1 | 7/2010 | Garakani |
| 2010/0324536 A1 | 12/2010 | Magnin et al. |
| 2011/0160834 A1 | 6/2011 | Aggerholm |
| 2012/0041470 A1 | 2/2012 | Shrivastava et al. |
| 2014/0180122 A1 | 6/2014 | Stigall et al. |

OTHER PUBLICATIONS

International Search Report and Written Opinion received in corresponding Patent Cooperation Treaty Application No. PCT/US2013/074176, dated Apr. 16, 2014, 4 pages.

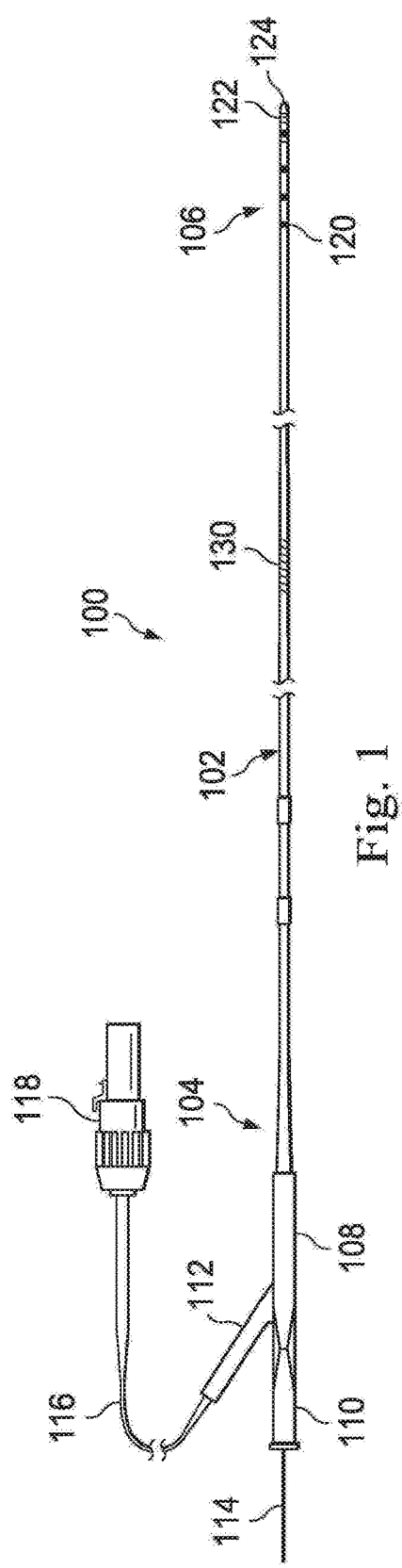
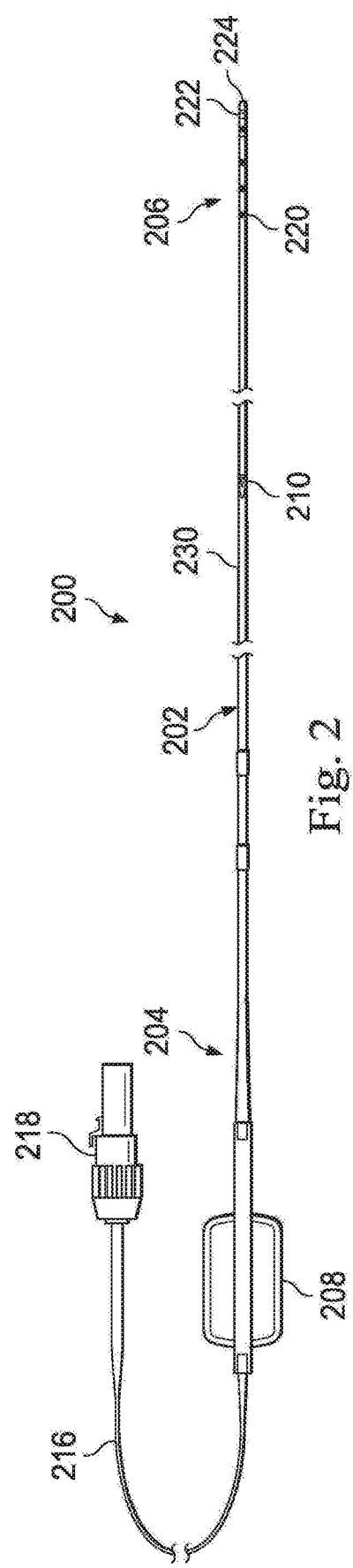
Fig. 1
Fig. 2

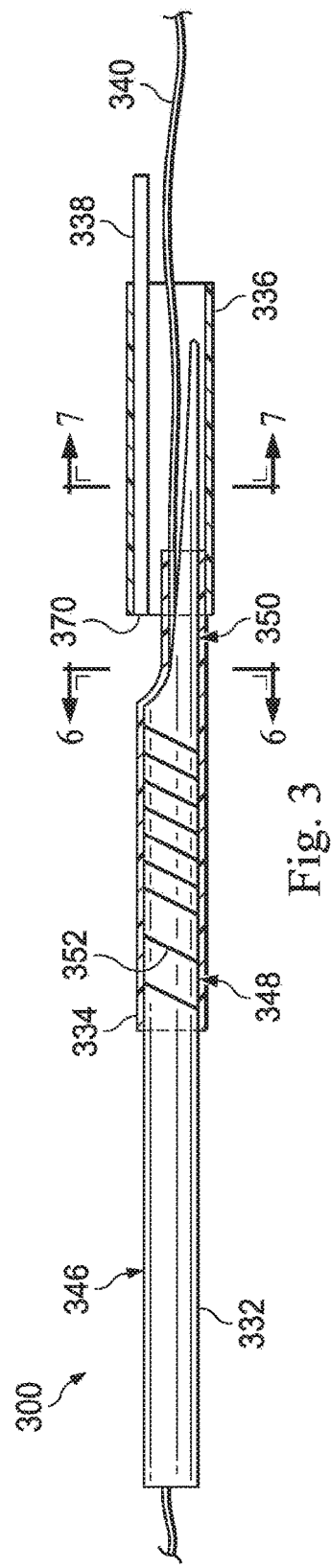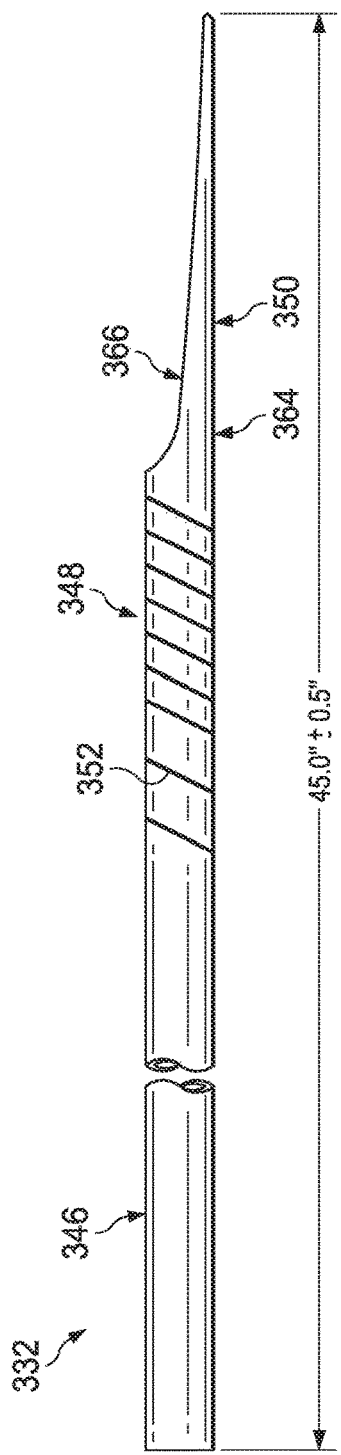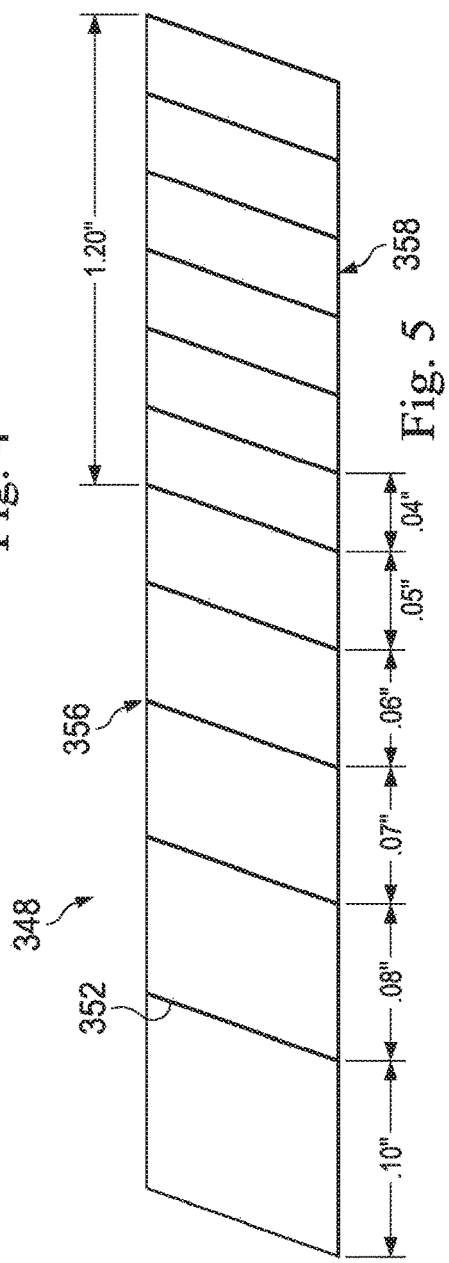

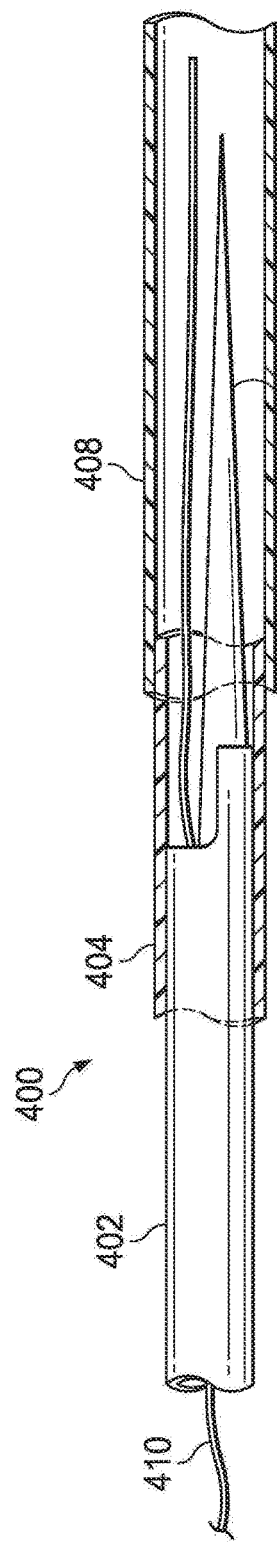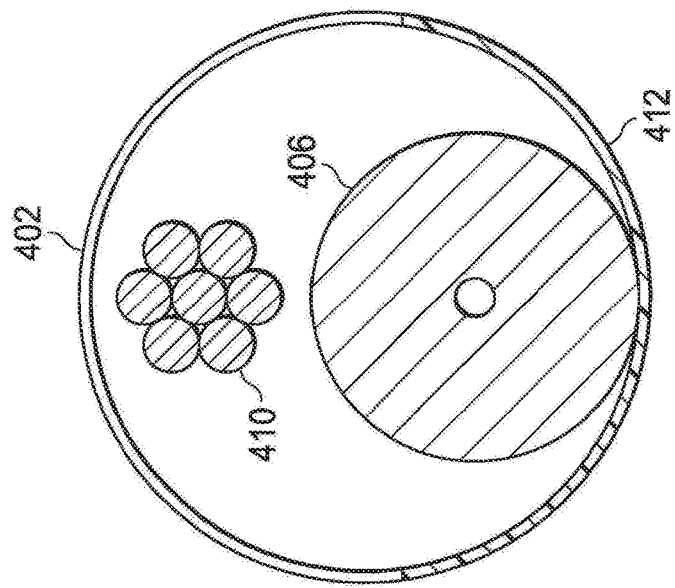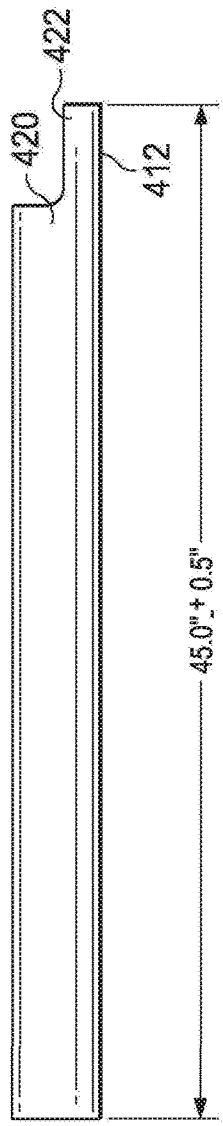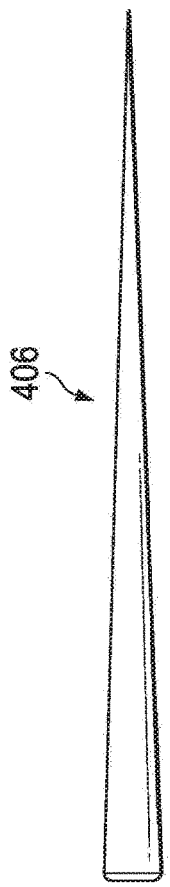

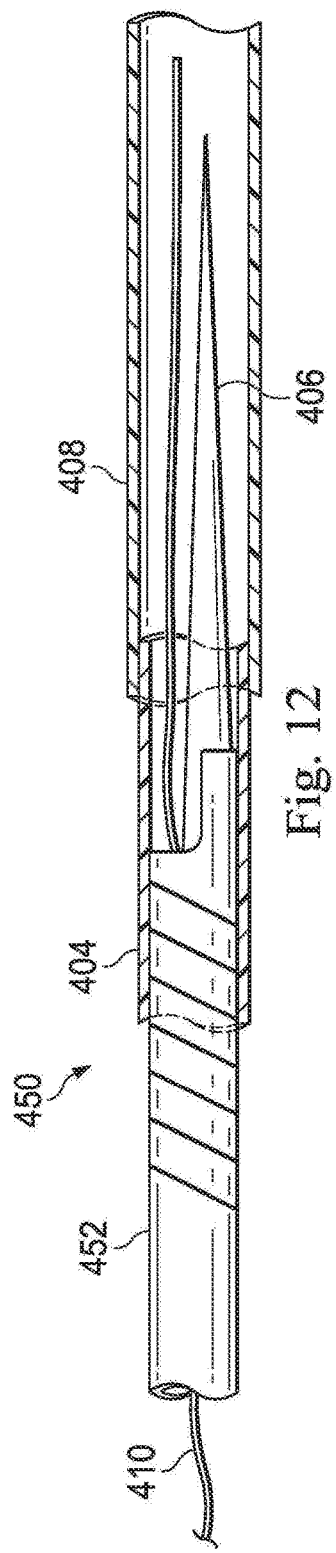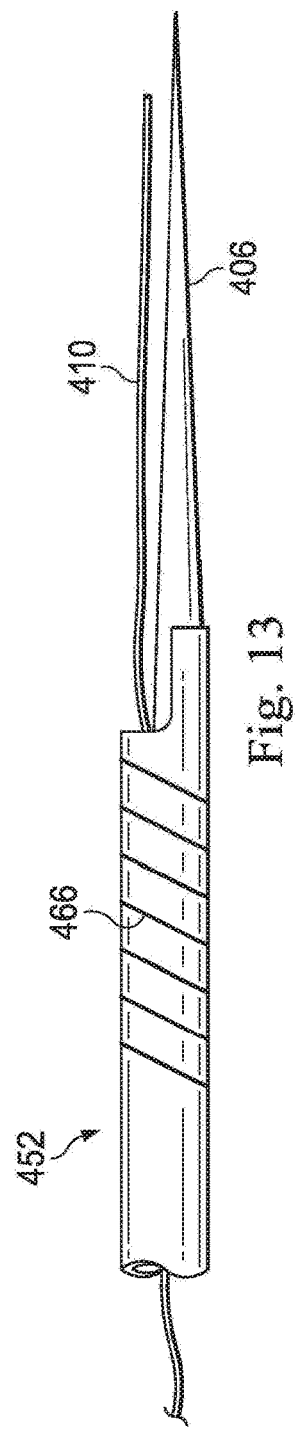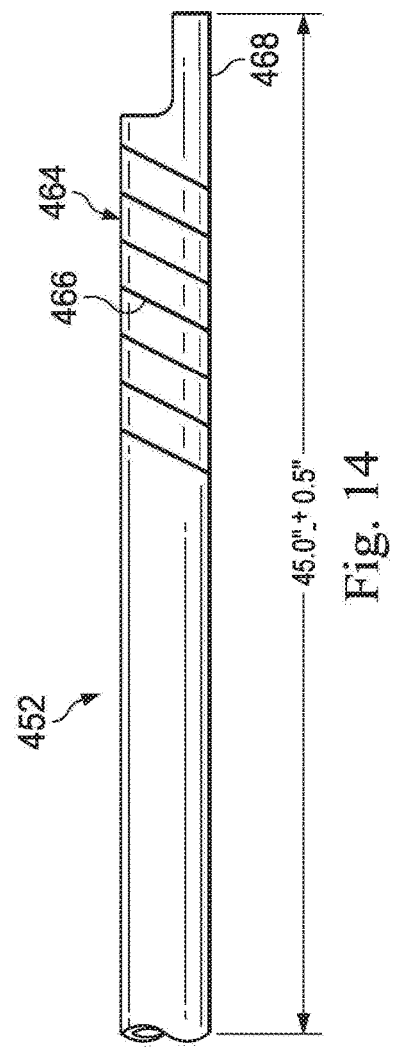

TRANSITIONAL REGION HAVING CUTS AND A SKIVE FOR AN IMAGING CATHETER

CROSS-REFERENCE TO RELATED APPLICATIONS

The present application is a continuation of U.S. application Ser. No. 15/800,655, filed Nov. 1, 2017, which is a continuation of U.S. application Ser. No. 14/103,532, filed Dec. 11, 2013, now U.S. Pat. No. 9,833,125, which claims priority to and the benefit of U.S. Provisional Patent Application No. 61/738,710, filed Dec. 18, 2012, U.S. Provisional Patent Application No. 61/738,831, filed Dec. 18, 2012, U.S. Provisional Patent Application No. 61/738,864, filed Dec. 18, 2012, and U.S. Provisional Patent Application No. 61/738,896, filed Dec. 18, 2012, each of which is hereby incorporated by reference in its entirety.

TECHNICAL FIELD

The present disclosure relates to intravascular devices, systems, and methods. In some aspects the present disclosure relates to intravascular devices, systems, and methods that include a transitional region connecting a stiffer proximal portion to a more flexible distal portion.

BACKGROUND

Intravascular ultrasound (IVUS) imaging systems have been designed for use by interventional cardiologists in the diagnosis and treatment of cardiovascular and peripheral vascular disease. Such systems enhance the effectiveness of the diagnosis and treatment by providing important diagnostic information that is not available from conventional x-ray angiography. This information includes the location, amount, and composition of arteriosclerotic plaque and enables physicians to identify lesion characteristics, select an optimum course of treatment, position therapeutic devices and promptly assess the results of treatment.

Such IVUS systems generally include an IVUS device having one or more miniaturized transducers mounted on the distal portion of a catheter or guide wire to provide electronic signals to an external imaging system. The external imaging system produces an image of the lumen of the artery or other cavity into which the catheter is inserted, the tissue of the vessel, and/or the tissue surrounding the vessel.

Before the development of less invasive approaches, the principal mode of treatment for occluded arteries was bypass surgery and, in the case of occlusions in the coronary arteries, coronary artery bypass surgery. Coronary artery bypass surgery is a highly invasive procedure in which the chest cavity is opened to expose the heart to provide direct surgical access to the coronary arteries. The procedure also includes the surgical removal of blood vessels from other locations in the patient's body (e.g., the sapheneous vein) which then are grafted surgically to the coronary arteries to bypass the occlusions. The recuperative period is lengthy with considerable discomfort to the patient.

The use of less invasive, catheter-based, intravascular techniques has developed for several decades and may be considered as the preferred mode of treatment for those patients amenable to such treatment. Typically, the intravascular procedures, such as angioplasty, atherectomy, and stenting require preliminary navigation of a guidewire through the patient's arteries to and through the occlusion. This guidewire, so placed, serves as a rail along which catheters can be advanced directly to and withdrawn from the target site. Total occlusions often cannot be treated with such minimally invasive intravascular approaches because of the inability to advance a guidewire through the stenosis. Typically patients with such occlusions have been treatable, if at all, by bypass surgery. Although in some instances, physicians may be able to force a guidewire through a total occlusion if the occluding material is relatively soft, attempts to force the guidewire through can present serious risks of perforating the artery. Arterial perforation can be life threatening.

As noted above, recently techniques and systems have been developed to visualize the anatomy of vascular occlusions by using intravascular ultrasound (IVUS) imaging. IVUS techniques are catheter-based and provide a real-time sectional image of the arterial lumen and the arterial wall. An IVUS catheter includes one or more ultrasound transducers at the distal portion of the catheter by which images containing cross-sectional information of the artery under investigation can be determined.

IVUS catheters typically include a distal portion that is more flexible than the proximal portion. The stiffer proximal portion provides some rigidity that may aid and simplify advancing the catheter into the patient by pushing the catheter from its proximal portion along the guidewire in the patient. The more flexible distal portion is configured to wind through more tortious vasculature, such as a patient's coronary artery, than the proximal portion. A flexible distal portion may decrease the likelihood of tissue damage as the catheter advances along the guidewire.

Because of the relatively large difference in stiffness, the intersection of the proximal and distal ends of the IVUS catheter may be prone to bending or kinking. Accordingly, when the proximal portion of the IVUS catheter is pushed to advance the catheter through the patient's vasculature, in some instances, the catheter can bend or kink. In some of these instances, a kinked catheter may no longer be suitable for completing the procedure or it may present health risks to the patient. Accordingly, in some cases, it must be withdrawn from the patient, discarded, and replaced with a new catheter. Conventional catheters lack the distal transducers discussed above that are included in imaging catheters. In order to communicate images or other data from the transducers to an image display system, electrical cables extend form the transducer through the catheter. Accordingly, the intersection of the proximal and distal portions should not only withstand introduction to the patient without being damaged, but should accommodate the cable in a way that does not interfere with standard operation of the IVUS or other imaging catheter.

Accordingly, there remains a need for improved devices, systems, and methods for visualizing vessels having a severe blockage or other restriction to the flow of fluid through the vessel. The present disclosure addresses one or more of the problems in the prior art.

SUMMARY

In an exemplary aspect, the present disclosure is directed to an imaging device for imaging a portion of a patient's vasculature with an imaging element. The imaging device may include a proximal portion having a relatively higher stiffness that provides rigidity for pushing the imaging device through a patient's vasculature, and may include a distal portion having a relatively lower stiffness that enables threading through a curved vasculature of the patient. The imaging device also may include a transition region disposed between the proximal portion and the distal portion. The transition region may have a graduated stiffness transitioning from the stiffness of the proximal portion to the stiffness of the distal portion. The transition region may include a hypotube having a skive formed at a distal end thereof, the skive having a connection region and a tapered portion. The skive connection region may smoothly connect the skive to the hypotube and the tapered portion may extend distally of the connection region. The tapered portion may be relatively more stiff at a proximal region and less stiff at a distal region.

In an aspect, the device includes a microcable extending through the proximal portion, the transition region, and the distal portion, the microcable being arranged to carry imaging signals from the distal region, the microcable being embedded within the distal portion. In an aspect, a distal shaft and an inner member are embedded within the outer distal shaft, the inner member being configured to receive a guidewire, the microcable being disposed between the skive and the inner member. In an aspect, the inner member has an opening end in the transition region. In an aspect, the microcable lies within the skive. In an aspect, the tapered portion comprises a skive proximal region and a skive distal region, the skive proximal region having a first cross-sectional area and the skive distal region having second cross-sectional area, the first cross-sectional region being larger than the second cross-sectional region such that the skive proximal region has a greater stiffness than the skive distal region.

In another exemplary aspect, the present disclosure is directed to an imaging device for imaging a portion of a patient's vasculature with an imaging element. The imaging device may include a proximal portion having a relatively higher stiffness that provides rigidity for pushing the imaging device through a patient's vasculature, and may include a distal portion having a relatively lower stiffness that enables threading through a curved vasculature of the patient. A transition region may be disposed between the proximal portion and the distal portion. The transition region may have a graduated stiffness transitioning from the stiffness of the proximal portion to the stiffness of the distal portion. The transition region may comprise a hypotube having one or more cuts formed therein to decrease the rigidity of the hypotube, the one or more cuts being spaced along the hypotube to create segments between the one or more cuts that vary in length when measured longitudinally along the imaging device, the segments having a greater length at a more proximal portion and a shorter length at a more distal portion.

In an aspect, the hypotube comprises a skive formed at a distal end thereof, the skive having a skive proximal region and a skive distal region, the skive proximal region having a first cross-sectional area and the skive distal region having second cross-sectional area, the first cross-sectional region being larger than the second cross-sectional region such that the skive proximal region has a greater stiffness than the skive distal region. In an aspect, an outer distal shaft portion forms a part of the transition region, the outer distal shaft portion extending over the skive distal region to provide a graduated flexibility transition from the skive to the distal portion. In an aspect, a microcable extends through the proximal portion, the transition region, and the distal portion, the microcable being arranged to carry imaging signals from the distal region, the microcable being embedded within the distal portion.

In another exemplary aspect, the present disclosure is directed to an imaging device for imaging a portion of a patient's vasculature with an imaging element. The device may include a proximal portion having a relatively higher stiffness that provides rigidity for pushing the imaging device through a patient's vasculature, and may include a distal portion having a relatively lower stiffness that enables threading through a curved vasculature of the patient. A transition region may be disposed between the proximal portion and the distal portion. The transition region may have a graduated stiffness transitioning from the stiffness of the proximal portion to the stiffness of the distal portion. The transition region may include a hypotube having a cut region at a distal portion formed one or more cuts formed therein to decrease the rigidity of the hypotube, the one or more cuts being spaced along the hypotube to create segments between the one or more cuts that vary in length when measured longitudinally along the imaging device, the segments having a greater length at a more proximal portion and a shorter length at a more distal portion. The hypotube may include a skive formed distally of the cut region, the skive having a skive proximal region and a skive distal region, the skive proximal region having a first cross-sectional area and the skive distal region having second cross-sectional area, the first cross-sectional region being larger than the second cross-sectional region such that the skive proximal region has a greater stiffness than the skive distal region, the skive being formed to have more flexibility than the cut region. A microcable may extend through the proximal portion, through the cut portion of the transition region, along the skive of transition region, and to the distal portion, the microcable being arranged to carry imaging signals from the distal region, the microcable being embedded within the flexible distal portion.

In an aspect, an outer distal shaft and an inner member are embedded within the outer distal shaft, the inner member being configured to receive a guidewire, the microcable being disposed between the skive and the inner member.

In an exemplary aspect, the present disclosure is directed to an imaging device for imaging a portion of a patient's vasculature with an imaging element. The imaging device includes a proximal portion having a relatively higher stiffness that provides rigidity for pushing the imaging device through a patient's vasculature, a distal portion having a relatively lower stiffness that enables threading through a curved vasculature of the patient, and a transition region disposed between the proximal portion and the distal portion. The transition region may have a graduated stiffness transitioning from the stiffness of the proximal portion to the stiffness of the distal portion, and may include a hypotube, and a stiffening element fixedly secured to the hypotube and extending distally of the hypotube. The stiffening element may have a proximal region and a distal region, with the proximal region having a first higher stiffness and the distal region having a second lower stiffness. The stiffening element being arranged to transition the stiffness of the imaging device from the stiffness of the proximal portion to the stiffness of the distal portion.

In an aspect, the hypotube comprises a skive and the stiffening element is attached to and extends from the skive. In an aspect, a proximal end of the stiffening element is soldered to an inner surface of the skive. In an aspect, the skive comprises a protruding portion having a continuous cross-section. In an aspect, the stiffening element is a tube having a length of in the range of about 2 inch and 12 inch. In an aspect, the imaging device includes a microcable extending through the proximal portion, through the stiffening element, and through the distal portion, the microcable being arranged to carry imaging signals from the distal portion, and the microcable being embedded within the distal portion. In an aspect, the imaging device includes an outer distal shaft portion forming a part of the transition region, the outer distal shaft portion extending over a distal portion of the stiffening element to provide a graduated flexibility transition from the stiffening element to the distal portion. In an aspect, the stiffening element comprises a cut region configured to provide a reduction in stiffness in the distal direction. In an aspect, the cut region comprises a spiral cut creating segments of the hypotube having a longitudinal length. In an aspect, the spiral cut is graduated such that the spiral cut creates segments having a longitudinal length greater in the proximal direction and shorter in the distal direction. In an aspect, the spiral cut has a width that creates gaps or spaces between adjacent segments. In an aspect, the stiffening element also comprises a non-cut region, the non-cut region being formed to fit within a portion of the hypotube and the cut region extending distally of the hypotube. In an aspect, the cut region extends about 25% of the length of the stiffening element. In an aspect, the cut region extends about 2 inches and the non-cut region extends about 6 inches.

In an exemplary aspect of the present disclosure, the present disclosure is directed to an imaging device for imaging a portion of a patient's vasculature with an imaging element. The imaging device includes a proximal portion having a relatively higher stiffness that provides rigidity for pushing the imaging device through a patient's vasculature, a distal portion having a relatively lower stiffness that enables threading through a curved vasculature of the patient, and a transition region disposed between the proximal portion and the distal portion. The transition region may have a graduated stiffness transitioning from the stiffness of the proximal portion to the stiffness of the distal portion, and the transition region may include a hypotube having a skive formed at a distal end thereof and may include a stiffening element fixedly secured to the skive and extending distally of the skive. The stiffening element may include a proximal region and a distal region, the distal region comprising one or more cuts formed therein to decrease the rigidity of the stiffening element, such that the distal region has a stiffness less than a stiffness of the hypotube. In an aspect, the proximal region of the stiffening element is structurally configured to have a stiffness less than the stiffness of the hypotube and the distal region of the stiffening element is structurally configured to have a stiffness less than the stiffness of the proximal region of the stiffening element. In an aspect, the stiffening element is sized small enough to fit within a distal end of the hypotube. In an aspect, the stiffening element is a tube having a length of in the range of about 2 inch and 12 inch. In an aspect, the imaging device includes a microcable extending through the proximal portion, through the stiffening element, and through the distal portion, the microcable being arranged to carry imaging signals from the distal portion. In an aspect, the imaging device includes an outer distal shaft portion forming a part of the transition region, the outer distal shaft portion extending over a distal portion of the stiffening element to provide a graduated flexibility transition from the stiffening element to the distal portion. In an aspect, the one or more cuts comprises a spiral cut creating segments of the hypotube having a longitudinal length. In an aspect, the spiral cut is graduated such that the spiral cut creates segments having a longitudinal length greater in the proximal direction and shorter in the distal direction. In an aspect, the proximal region of the stiffening element comprises a non-cut region, the non-cut region being formed to fit within a portion of the hypotube and the cut region extending distally of the hypotube.

In an exemplary aspect, the present disclosure is directed to an imaging device for imaging a portion of a patient's vasculature with an imaging element. The imaging device includes a proximal portion having a relatively higher stiffness that provides rigidity for pushing the imaging device through a patient's vasculature, a distal portion having a relatively lower stiffness that enables threading through a curved vasculature of the patient, and a transition region disposed between the proximal portion and the distal portion. The transition region may have a graduated stiffness transitioning from the stiffness of the proximal portion to the stiffness of the distal portion, an may include a hypotube having a skive formed at a distal end thereof and a stiffening element fixedly secured to the skive and extending distally of the skive. The stiffening element may have a proximal region and a distal region, with the proximal region having a first higher stiffness and the distal region having a second lower stiffness. The stiffening element may be arranged to transition the stiffness of the imaging device from the stiffness of the proximal portion to the stiffness of the distal portion.

In an aspect, the stiffening element is a tapering stiffening wire having a length within a range of about 1-3 inches. In an aspect, the stiffening element is structurally configured so that the stiffness continuously and smoothly transitions from the first higher stiffness to the second lower stiffness. In an aspect, the imaging system comprises a microcable extending through the proximal portion, over the stiffening element, and through the distal portion. The microcable may be arranged to carry imaging signals from the distal portion, and may be embedded within the distal portion. In an aspect, the imaging device also includes a polymer jacket extending over a portion of the skive and the stiffness element, the polymer jacket maintaining the position of the microcable relative to the stiffening element. In an aspect, the hypotube further comprises a spiral cut configured to provide a reduction in stiffness in the distal direction. In an aspect, the spiral cut is graduated such that the spiral cut creates segments having a longitudinal length greater in the proximal direction and shorter in the distal direction. In an aspect, the spiral cut creates segments, the spiral cut having a thickness or width creating gaps or spaces between adjacent segments. In an aspect, the hypotube comprises a spaced spiral cut region and a non-spaced spiral cut region, the spaced spiral cut region having a wide cut such that segments are spaced apart and the non-spaced spiral cut region having a small cut such that segments abut against one another.

In an aspect, the present disclosure is directed to an imaging device for imaging a portion of a patient's vasculature with an imaging element. The imaging device includes a proximal portion having a relatively higher stiffness that provides rigidity for pushing the imaging device through a patient's vasculature, a distal portion having a relatively lower stiffness that enables threading through a curved vasculature of the patient, a transition region disposed between the proximal portion and the distal portion. The transition region having a graduated stiffness transitioning from the stiffness of the proximal portion to the stiffness of the distal portion. The transition region may include a hypotube having a skive formed at a distal end thereof, the hypotube having a cut region comprising one or more cuts formed therein to decrease the rigidity of the hypotube. The one or more cuts may be spaced along the hypotube to create segments between the one or more cuts that vary in length when measured longitudinally along the imaging device. The segments may have a greater length at a more proximal portion and a shorter length at a more distal portion. The transition region may also include a stiffening element fixedly secured to the skive and extending distally of the skive, the stiffening element having a stiffness less than the stiffness of the cut region of the hypotube.

In an aspect, the stiffening element is a tapering stiffening wire having a length within a range of about 1-3 inches. In an aspect, the imaging device may include a microcable extending through the proximal portion, over the stiffening element, and through the distal portion, the microcable being arranged to carry imaging signals from the distal portion, the microcable being embedded within the distal portion. In an aspect, the stiffening element is a solid stiffening element. In an aspect, the imaging device may include an outer distal shaft portion forming a part of the transition region, the outer distal shaft portion extending over a distal portion of the stiffening element to provide a graduated flexibility transition from the stiffening element to the distal portion. In an aspect, the spiral cut is graduated such that the one or more cuts creates segments having a longitudinal length greater in the proximal direction and shorter in the distal direction. In an aspect, the one or more cuts create segments, the one or more cuts having a thickness or width creating gaps or spaces between adjacent segments. In an aspect, the hypotube comprises a spaced spiral cut region and a non-spaced spiral cut region, the spaced spiral cut region having a wide cut such that segments are spaced apart and the non-spaced spiral cut region having a small cut such that segments abut against one another. In an aspect, the stiffening element comprises a proximal region and a distal region, the proximal region having a first higher stiffness and the distal region having a second lower stiffness, the stiffening element being arranged to transition the stiffness of the imaging device from the stiffness of the proximal portion to the stiffness of the distal portion.

In an exemplary aspect, the present disclosure is directed to an imaging device for imaging a portion of a patient's vasculature with an imaging element. The imageing device may include a proximal portion having a relatively higher stiffness that provides rigidity for pushing the imaging device through a patient's vasculature, a distal portion having a relatively lower stiffness that enables threading through a curved vasculature of the patient, and a transition region disposed between the proximal portion and the distal portion. The transition region may include a graduated stiffness transitioning from the stiffness of the proximal portion to the stiffness of the distal portion, and may also include a hypotube having a cylindrical portion and a tapering portion extending distally from the cylindrical portion. The cylindrical portion may have a first stiffness and the tapering portion may have a second stiffness that decreases from the cylindrical portion in the distal direction to transition the stiffness of the imaging device from the stiffness of the proximal portion to the stiffness of the distal portion.

In an aspect, the imaging device also includes an imaging transducer disposed in the distal portion, and a microcable extending through the proximal portion, through the transition region, and through the distal portion, the microcable being arranged to carry imaging signals captured at the distal portion. In an aspect, the tapering portion is a conical portion. In an aspect, the tapering portion is a hollow portion comprising a solid tapering region and a cut region, the solid tapering region being disposed proximal the cut region, the cut region being configured to provide a reduction in stiffness in the distal direction. In an aspect, the cut region comprises a spiral cut creating segments of the hypotube having a longitudinal length.

In another exemplary aspect, the present disclosure is directed to an imaging device for imaging a portion of a patient's vasculature with an imaging element. The imaging device may include a proximal portion having a relatively higher stiffness that provides rigidity for pushing the imaging device through a patient's vasculature, a distal portion having a relatively lower stiffness that enables threading through a curved vasculature of the patient, and a a transition region disposed between the proximal portion and the distal portion. The transition region may have a graduated stiffness transitioning from the stiffness of the proximal portion to the stiffness of the distal portion. The transition region may include a hypotube having a cylindrical portion and a tapering portion extending distally from the cylindrical portion. The tapering portion may have a solid tapering region forming a proximal region of the tapering portion and a structural flexibility enhancer region forming a distal region of the tapering portion. The cylindrical portion having a first stiffness and the proximal region of the tapering portion having a stiffness that decreases from the cylindrical portion in the distal direction and the distal region of the tapering portion having a stiffness that decreases from the proximal region of the tapering portion to transition the stiffness of the imaging device from the stiffness of the proximal portion to the stiffness of the distal portion.

In an aspect, the imaging device includes an imaging transducer disposed in the distal portion and a microcable extending through the proximal portion, through the transition region, and through the distal portion, the microcable being arranged to carry imaging signals captured at the distal portion. In an aspect, the flexibility enhancer is a cut region. In an aspect, the proximal region of the tapering portion is a hollow, solid tapering region and the distal region of the tapering portion is the cut region, the cut region comprising one or more spiral cuts creating segments of the hypotube having a longitudinal length. In an aspect, the one or more spiral cuts is graduated such that the spiral cut creates segments having a longitudinal length greater in the proximal direction and shorter in the distal direction. In an aspect, one or more the spiral cuts has a width that creates gaps or spaces between adjacent segments. In an aspect, the cut region extends about 25% of the length of the stiffening element. In an aspect, the imaging device includes a polymer jacket disposed over at least a portion of the tapering portion, the polymer jacket matching the profile of the tapering portion.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

Illustrative embodiments of the present disclosure will be described with reference to the accompanying drawings, of which:

FIG. 1 is a diagrammatic perspective view of an imaging device according to an exemplary embodiment of the present disclosure.

FIG. 2 is a diagrammatic perspective view of an imaging device according to another embodiment of the present disclosure.

FIG. 3 illustrates a side view of a transition region of an imaging device according to an exemplary aspect of the present disclosure.

FIG. 4 illustrates a side view of an exemplary hypotube of the transition region of FIG. 3 according to an exemplary aspect of the present disclosure.

FIG. 5 illustrates a side view of a portion of an exemplary hypotube of the transition region of FIG. 3 according to an exemplary aspect of the present disclosure.

FIG. 8 illustrates a side view of a transition region of an imaging device according to an exemplary aspect of the present disclosure.

FIG. 9 illustrates a side view of an exemplary hypotube of the transition region of FIG. 8 according to an exemplary aspect of the present disclosure.

FIG. 10 illustrates a side view of an exemplary stiffening element of the transition region of FIG. 8 according to an exemplary aspect of the present disclosure.

FIG. 11 illustrates an end view showing selected elements of FIG. 8 according to an exemplary aspect of the present disclosure.

FIG. 12 illustrates a side view of a transition region of an imaging device according to an exemplary aspect of the present disclosure.

FIG. 13 illustrates a side view of selected elements of the transition region of FIG. 12 according to an exemplary aspect of the present disclosure.

FIG. 14 illustrates a side view of a portion of an exemplary hypotube of the transition region of FIG. 12 according to an exemplary aspect of the present disclosure.

DETAILED DESCRIPTION

Figure 7:
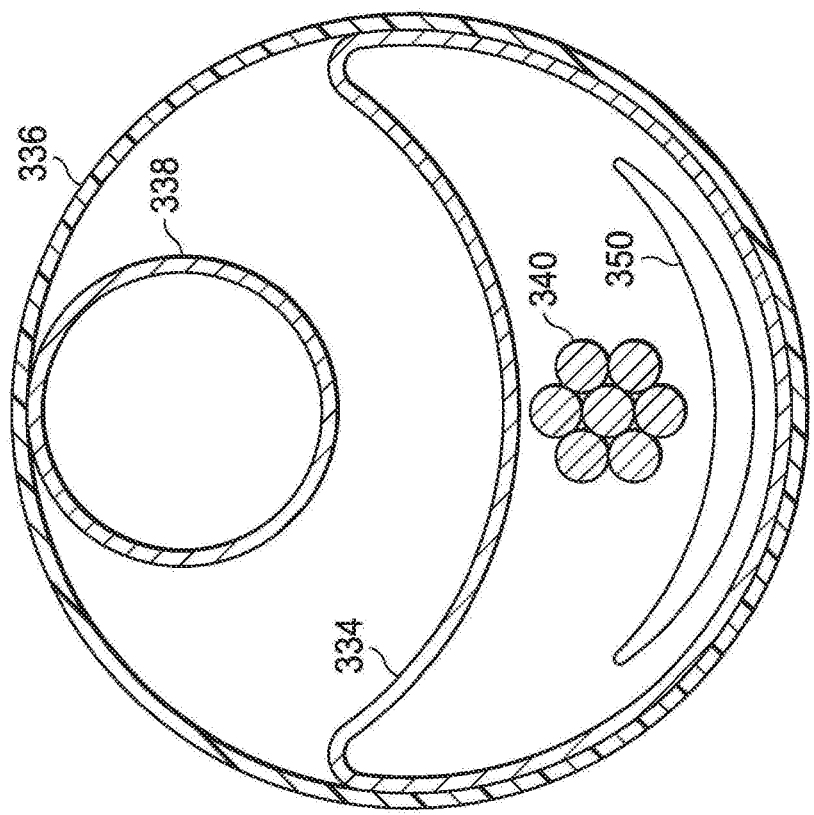
FIG. 7 illustrates a cross-sectional view taken along lines 7-7 in FIG. 3 according to an exemplary aspect of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any connections and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

As used herein, "flexible elongate member" or "elongate flexible member" includes at least any thin, long, flexible structure that can be inserted into the vasculature of a patient. While the illustrated embodiments of the "flexible elongate members" of the present disclosure have a cylindrical profile with a circular cross-sectional profile that defines an outer diameter of the flexible elongate member, in other instances all or a portion of the flexible elongate members may have other geometric cross-sectional profiles (e.g., oval, rectangular, square, elliptical, etc.) or non-geometric cross-sectional profiles. Flexible elongate members include, for example, guide wires and catheters. In that regard, catheters may or may not include a lumen extending along its length for receiving and/or guiding other instruments. If the catheter includes a lumen, the lumen may be centered or offset with respect to the cross-sectional profile of the device.

The devices and systems disclosed herein include a relatively more stiff proximal portion and a relatively less stiff distal portion. A transition region separates these and aids in transitioning from the more stiff proximal portion to the less stiff distal portion. The transition region is structured to form a gradual change in stiffness, rather than a single abrupt change in stiffness. This gradual change in stiffness may provide multiple advantages over systems with a single abrupt change in stiffness. For example, systems and devices having a gradual change in stiffness may be more easily introduced through the vasculature, may have a decreased incidence of kinking, and may have increased trackability. This directly contributes to predictability and consistency in the surgical room, contributing to surgeon satisfaction and potentially better patient outcome.

FIG. 1 shows an imaging device 100 according to an exemplary embodiment of the present disclosure. As shown, the imaging device 100 comprises an elongate flexible body 102 having a proximal portion 104 and a distal portion 106. The proximal portion 104 includes an adapter 108. In the illustrated embodiment, the adapter 108 is y-shaped with extensions 110 and 112. In that regard, extension 110 generally extends along the longitudinal axis of the body 102, while extension 112 extends at an oblique angle with respect to the longitudinal axis of the body. Generally, the extensions 110 and 112 provide access to the body 102. In that regard, in the illustrated embodiment extension 110 is configured to receive a guidewire 114 that is sized and shaped to fit within a lumen that extends along the length of the body 102 from the proximal portion 104 to the distal portion 106 and defines an opening at the distal end of the imaging device 100. As a result of this arrangement, the imaging device 100 is understood to be what is commonly referred to as an over-the-wire catheter. In some embodiments, the lumen of the imaging device is centered about the central longitudinal axis of the body 102. In other embodiments, the lumen is offset with respect to the central longitudinal axis of the body 102.

In the illustrated embodiment, extension 112 of adapter 108 is configured to receive communication lines (e.g., electrical, optical, and/or combinations thereof) that are coupled to imaging components positioned within the distal portion 106 of the imaging device 100. In that regard, a cable 116 containing one or more communication lines extends from extension 112 to a connector 118. The connector 118 is configured to interface the imaging device directly or indirectly with one or more of a patient interface module ("PIM"), a processor, a controller, and/or combinations thereof. The particular type of connection depends on the type of imaging components implemented in the imaging device, but generally include one or more of an electrical connection, an optical connection, and/or combinations thereof.

The distal portion 106 includes a main body the contains imaging components, such as the imaging element 122, which may include various electronic, optical, and/or electro-optical components necessary for the particular imaging modality utilized by the imaging device. In the illustrated embodiment, the distal portion 106 of the imaging device is configured for ultrasound imaging and includes an array of ultrasound transducers arranged circumferentially about the distal portion 300 of the imaging device. The main body of the distal portion 106 has a diameter or thickness that closely matches the diameter of the proximal portion 104 of the imaging device. In some instances, the diameter or thickness of the distal portion 106 exactly matches the diameter of the proximal portion 104 of the imaging device. In other instances, the diameter or thickness of the distal portion 106 is slightly larger or slight smaller than the diameter of the proximal portion 104 of the imaging device. In some instances, the diameter or thickness of the distal portion is between about 0.5 mm and about 5 mm, with some particular embodiments having a diameter or thickness of 2.73 mm (8.2 French), 2.33 mm (7 French), 1.17 mm (3.5 French), 1.1 mm (3.3 French), 1.0 mm (3 French), 0.97 mm (2.9 French), or otherwise.

The distal portion 106 includes a plurality of markers 120. In that regard, the markers 120 are visible using non-invasive imaging techniques (e.g., fluoroscopy, x-ray, CT scan, etc.) to track the location of the distal portion 106 of the imaging device 100 within a patient. Accordingly, in some instances the markers 120 are radiopaque bands extending around the circumference of the body 102. Further, the markers 120 are positioned at known, fixed distances from an imaging element 122 and/or the distal end 124 of the imaging device 100 in some instances. While the distal portion 106 has been illustrated and described as having a plurality (two or more) of markers 120, in other embodiments the distal portion 106 includes one marker or no markers. Further, in some embodiments, one or more components associated with the imaging element 122 can be utilized as a marker to provide a reference of the position of the distal portion 106 of the imaging device 100.

The imaging element 122 may be any type of imaging element suitable for visualizing a vessel and, in particular, a sever occlusion in a vessel. Accordingly, the imaging element may be an ultrasound transducer array (e.g., arrays having 16, 32, 64, or 128 elements are utilized in some embodiments), a single ultrasound transducer, one or more optical coherence tomography ("OCT") elements (e.g., mirror, reflector, and/or optical fiber), and/or combinations thereof. In that regard, in some embodiments the imaging device 100 is configured to be rotated (either manually by hand or by use of a motor or other rotary device) to obtain images of the vessel.

In the exemplary embodiment shown, the elongate flexible body 102 also includes a transition region 130 between the proximal portion 104 and the distal portion 106. The transition region 130 provides a gradual change in rigidity from the stiffer proximal portion 104 to the more flexible distal portion 106. This gradual shift from more rigid to more flexible may enable more consistent advancement of the flexible body 102 through the tortious intravascular system with a reduced likelihood of kinking. Accordingly, there is more predictability and a reduced chance of a wasted or ineffective imaging device. In the embodiments shown, the transition region 130 is disposed closer to the distal end 124 than the adapter 108. In some embodiments, the transition region 130 is particularly suited for imaging of a heart and may be disposed a distance between about 20 cm to 30 cm from the distal end 124.

Referring to FIG. 2, shown therein is an imaging device 200 according to another embodiment of the present disclosure. As shown, the imaging device 200 comprises an elongate flexible body 202 having a proximal portion 204 and a distal portion 206. The proximal portion 204 includes a handle 208 for grasping by a user. In the illustrated embodiment, a cable 216 extends from the handle 208 and includes one or more communication lines (e.g., electrical, optical, and/or combinations thereof) that are coupled to imaging components positioned within the distal portion 206 of the imaging device 200. In that regard, a cable 216 containing one or more communication lines extends from handle 208 to a connector 218. The connector 218 is configured to interface the imaging device directly or indirectly with one or more of a patient interface module ("PIM"), a processor, a controller, and/or combinations thereof. The particular type of connection depends on the type of imaging components implemented in the imaging device, but generally include one or more of an electrical connection, an optical connection, and/or combinations thereof.

The body 202 includes an opening 210 that is in communication with a lumen that extends along the length of the body 202 from the opening 210 to the distal portion 206 and defines an opening at the distal end of the imaging device 200. The opening 210 and the lumen it is in communication with are configured to receive a guidewire. As a result of this arrangement, the imaging device 200 is understood to be what is commonly referred to as a rapid exchange catheter. In some embodiments, the lumen of the imaging device is centered about the central longitudinal axis of the body 202. In other embodiments, the lumen is offset with respect to the central longitudinal axis of the body 202.

The distal portion 206 includes a plurality of markers 220. In that regard, the markers 220 are visible using non-invasive imaging techniques (e.g., fluoroscopy, x-ray, CT scan, etc.) to track the location of the distal portion 206 of the imaging device 200 within a patient. Accordingly, in some instances the markers 220 are radiopaque bands extending around the circumference of the body 202. Further, the markers 220 are positioned at known, fixed distances from an imaging element 222 and/or the distal end 224 of the imaging device 200 in some instances. While the distal portion 106 has been illustrated and described as having a plurality (two or more) of markers 220, in other embodiments the distal portion 206 includes one marker or no markers. Further, in some embodiments, one or more components associated with the imaging element 222 can be utilized as a marker to provide a reference of the position of the distal portion 206 of the imaging device 200.

The imaging element 222 may be any type of imaging element suitable for visualizing a vessel and, in particular, a sever occlusion in a vessel. Accordingly, the imaging element may be an ultrasound transducer array (e.g., arrays having 16, 32, 64, or 128 elements are utilized in some embodiments), a single ultrasound transducer, one or more optical coherence tomography ("OCT") elements (e.g., mirror, reflector, and/or optical fiber), and/or combinations thereof. In that regard, in some embodiments the imaging device 200 is configured to be rotated (either manually by hand or by use of a motor or other rotary device) to obtain images of the vessel.

In the exemplary embodiment shown, the elongate flexible body 202 also includes a transition region 230 between the proximal portion 204 and the distal portion 206. The transition region 230 provides a gradual change in rigidity from the stiffer proximal portion 204 to the more flexible distal portion 206. This gradual shift from more rigid to more flexible may enable more consistent advancement of the flexible body 202 through the tortious intravascular system with a reduced likelihood of kinking. Accordingly, there is more predictability and a reduced chance of a wasted or ineffective imaging device. In the embodiments shown, the transition region 230 is disposed closer to the distal end 224 than the handle 208. In some embodiments, the transition region 230 is particularly suited for imaging of a heart and may be disposed a distance between about 20 cm to 30 cm from the distal end 124.

Figure 23:
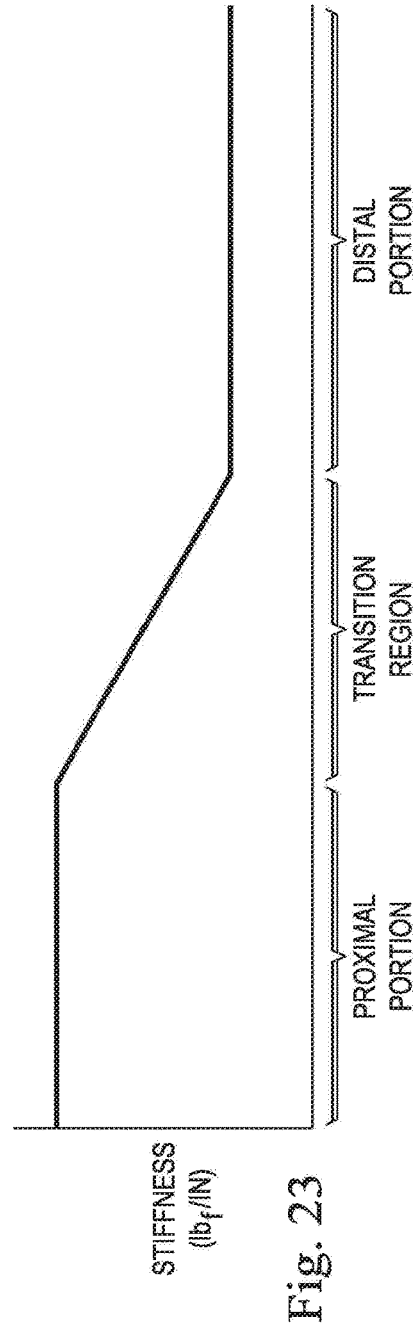
FIG. 23 is a graph illustrating a relative stiffness comparison of a proximal portion, a transition region, and a distal portion of an imaging device according to an exemplary embodiment of the present disclosure.

FIG. 23 shows an exemplary graph illustrating the relative stiffness of the flexible bodies 102, 202 discussed above. As can be seen in FIG. 23, the proximal portion, representing proximal portions 104, 204 has a first higher stiffness, and the distal portion, representing distal portions 106, 206, includes a second lower stiffness. The transition region, representing the transition regions 130, 230, is disposed between the proximal and distal portions and provides a transitional stiffness from the proximal portion to the distal portion. In the exemplary graph in FIG. 23, the transition region provides a continuous linear stiffness transition from the proximal portion stiffness to the distal portion stiffness. However, other embodiments include a stepped transition, a non-linear or curved transition, or other transitions. Some include combinations of these. However, all of the transition regions are gradual to provide more continuity in stiffness and to reduce the likelihood of kinking.

FIG. 3 shows an exemplary transition region referenced herein as 300 that may form the transition regions 130, 230 identified above. For ease of explanation, the transition region 300, as well as the other transition regions disclosed herein, will be described with reference to the embodiment of the imaging device 200 of FIG. 2, recognizing that the transition region may be likewise disposed as a part of the imaging device 100 in FIG. 1.

FIG. 3 shows the exemplary transition region 300 with some elements in partial transparency in order to display the different components of the transition region. The transition region includes a portion of a hypotube 332, a polymer jacket 334, an outer distal shaft 336, an inner member 338, and a microcable 340. Each of these are discussed in greater detail below and cooperate to provide a gradual transition from the stiffer proximal portion 204 to the more flexible distal portion 206.

The microcable 340 is a flexible cable extending from the proximal end of the imaging device 200 to the distal end 224 of the imaging device 200 for operation of the imaging element 222 at the distal end 224 of the device 200. The microcable 340 is formed of one or more conductors or fibers that carry signals to and from the imaging element 222 of the imaging device 200. In some embodiments, the microcable 340 is more flexible than the remaining materials making up the proximal portion and therefore adds little in the way of stiffness.

Figure 6:
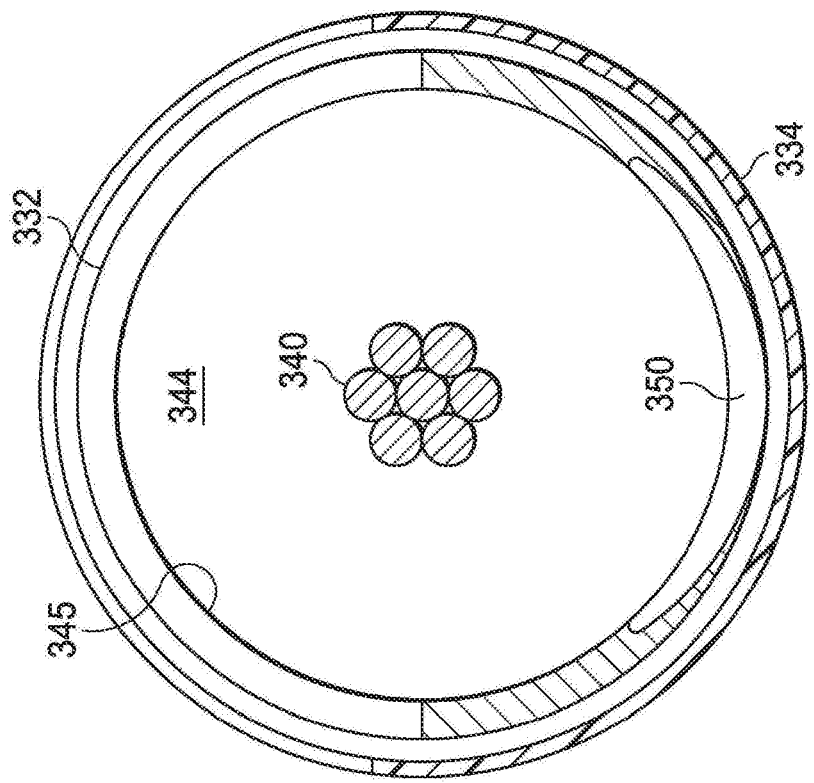
FIG. 6 illustrates a cross-sectional view taken along lines 6-6 in FIG. 3 according to an exemplary aspect of the present disclosure.

FIG. 6 shows an exemplary cross-sectional view taken along the lines 6-6 through the transition region 300 in FIG. 3. The microcable 340 can be seen in the cross-sectional view of FIG. 6. As can be seen, the microcable 340 includes one or more elements forming a communication medium, such as electrical conductors or optical fibers. These extend within the hypotube 332 and connect the imaging element 222 to a processing system (not shown) at the proximal end of the catheter 200. In one aspect, the imaging element 222 is an ultrasound transducer array having a maximum outer diameter of 0.045 in (3.5 F) and the microcable 340 includes a braided exterior with seven individual insulated electrical conductors. In another aspect, the microcable 340 comprises fiberoptics. In some embodiments, the microcable 340 extends through substantially the entire length of the imaging device 200 and joins the imaging element 222 and the processing system. The processing system typically remains outside of the patient. The processing system uses the data received from the imaging element 222. The imaging element 222 forms a part of an imaging system and data communicated over the microcable 340 can be used to create an image. The image can be displayed to a medical professional in real time as the catheter or imaging device 200 moves through the patient's artery. This allows the medical professional to find various occlusions or other irregularities which may exist throughout the patient's artery. In a similar manner, the imaging element 222 could be a pressure or flow sensor, and the processing system could determine fractional flow reserve values based on the sensed data.

The microcable may include any of a variety of types of communication elements that may run through the proximal and distal portions 204, 206 of the imaging device. For example, in the case that the imaging element 222 produces electrical signals to be processed by external systems, then the microcable 340 may include conductive wires to carry those electrical signals. Alternatively, the microcable 340 may include fiber optic cables to propagate those signals in the form of light. The number of wires or communication elements depends on the type of sensing device and the manner in which data is transferred from the sensing device to the external processing systems. Conductive wires may also be used to provide electrical power to the sensing device.

In the case that the imaging element 222 is a rotational imaging element, the microcable 340 may include a driveshaft lumen (not shown). In one aspect, the driveshaft lumen may include a plastic sheath filled with a liquid lubricant. The lubricant allows the driveshaft running through the plastic sheath to spin with a minimal amount of friction against the interior of the plastic sheath.

The imaging element 222 can be used to image the interior of a patient's artery. Various types of imaging elements may be used. One example of an imaging element 222 is an OCT device. In another form, the sensor can collect information for spectroscopy or photo acoustic imaging. The imaging element 222 may also be a forward looking device that scans forward into the artery rather than outward from the axis towards the arterial walls.

The imaging element 222 may also be an IVUS device. There are two general types of IVUS devices that may be used. The first type of device is a solid state device, also known as a phased array. Solid-state IVUS devices carry a transducer complex that includes an array of ultrasound transducers distributed around the circumference of the device. The transducers are connected to a set of transducer controllers. The transducer controllers select individual transducers for transmitting an ultrasound pulse and for receiving the echo signal. By stepping through a sequence of transmit-receive pairs, the solid-state IVUS system can synthesize the effect of a mechanically scanned transducer element, but without moving parts. Because there is no rotating mechanical element, the transducer array can be placed in direct contact with the blood and vessel tissue with minimal risk of vessel trauma. Furthermore, the interface is simplified because there is no rotating element. The solid-state scanner can be wired directly to the imaging system with a simple electrical cable and a standard detachable electrical connector.

In the example of a transducer array as an imaging element, the microcable 340 running through the catheter shafts includes the electrical cables that communicate data between the transducer array and external processing systems. The number of wires and cables comprising the connection media may depend on the type of transducer array. For example, a 64 bit array may use more cables than a 32 bit array. Additionally, various multiplexing functions may be used to reduce the number of wires running through the catheter shafts.

The second general type of IVUS device is a rotational device. A typical rotational IVUS device includes a single ultrasound transducer element located at the tip of a flexible driveshaft. The driveshaft spins inside a plastic sheath inserted into the vessel of interest. The transducer element is oriented such that the ultrasound beam propagates generally perpendicular to the axis of the device. The fluid-filled sheath protects the vessel tissue from the spinning transducer and driveshaft while permitting ultrasound signals to propagate from the transducer into the tissue and back. As the driveshaft rotates, the transducer is periodically excited with a high voltage pulse to emit a short burst of ultrasound. The same transducer then listens for the returning echoes reflected from various tissue structures. The IVUS imaging system assembles a two dimensional display of the vessel cross-section from a sequence of pulse/acquisition cycles occurring during a single revolution of the transducer.

The hypotube 332 is shown in FIG. 4 and forms at least a large portion of the proximal portion 204 and extends between the area of the handle 208 to the transition region 300. In some embodiments, the hypotube has a length between 34 in and 65 in, while in other embodiments, the hypotube 332 has a length of about 35-55 in, and in the embodiment, shown, the hypotube has a length of about 45 in. Other sizes, both larger and smaller than that mentioned are contemplated. The hypotube 332 may be formed of any rigid material, and in some embodiments, is formed of a stainless steel material. It has a hollow center 344 formed by an inner surface 345 (shown in FIG. 6). In some embodiments, the hypotube 332 has an outer diameter sized smaller than about 0.05 in. In some embodiments, the hypotube 332 has a diameter sized less than 0.03 in, and in some embodiments, the diameter is less than 0.025 in. The inner diameter may be less than about 0.04 in, and in some embodiments, is less than about 0.02 in, and in one embodiment, is about 0.015 in. In this example, the hypotube 332 is formed so that its rigidity gradually transitions from the stiffer proximal portion 104 toward the distal portion 106.

In the embodiment shown, the hypotube 332 includes a solid region 346, a spiral cut region 348, and a tapered skive 350. The solid region 346 forms the proximal end of the hypotube 332 and is the stiffest region of the hypotube 332. It provides rigidity to the elongate flexible body 102 enabling the surgeon to feed the elongate flexible body 202 into a patient.

The spiral cut region 348 extends the solid region 346 toward the tapered skive 350 and forms a part of the transition region 300. A spiral cut 352 in the spiral cut region 348 is arranged to impart mobility and increased flexibility to the distal end of the hypotube 332. In this embodiment, the spiral cut region 348 is formed of a cut 352 through the surface of the hypotube 332. In some embodiments, the cut 352 extends through the outer surface of the hypotube 332 to the inner surface 345 forming the hollow center 344. In other embodiments, the spiral cut 352 extends radially inwardly only through the outer surface of the hypotube 332, but does not cut through the inner surface 345 of the hypotube. This provides increased flexibility to the end of the hypotube 332 while at the same time limiting the amount of flexibility.

In this example, the spiral cut 352 includes a graduated spiral cut portion 356 and an equally spaced spiral cut portion 358. These can be seen best in FIG. 5. The spiral cut 352 divides the spiral cut region 348 into a plurality of segments. These can be measured linearly along the longitudinal direction as the distance between adjacent cuts. In the embodiment shown, the graduated spiral cut portion 356 includes a plurality of segments formed so that the distance between adjacent cuts decreases toward the distal direction. That is, the segments closer to the distal end of the hypotube 332 have a length less than the segments further from the distal end of the hypotube 332.

FIG. 5 shows a close up the spiral cut region 348 with dimensional values for segments shown. In some embodiments, the spiral cut region 348 extends for a linear distance along the longitudinal direction between about 0.5 and 3.5 in. In some embodiments, the spiral cut region 348 extends along the axis a distance between about 1.0 and 4.0 in. Other distances however, are contemplated.

In the exemplary embodiment shown, the graduated spiral cut portion 356 of the spiral cut region 348 includes a proximal-most segment having a distance between cuts of about 0.10 in. As can be seen, in this embodiment in FIG. 5, the distance or length of the segment between the next adjacent cuts is about 0.08 in, the distance between the next adjacent cuts is about 0.07 in, the distance between the next adjacent cuts is about 0.06 in, and so on.

The equally spaced spiral cut portion 358 includes segments that are equally spaced. In the embodiment shown, these may be spaced a distance of about 0.04 in, although other distances are contemplated. Since the segments in the equally spaced spiral cut portion 358 are closer together than those in the graduated spiral cut portion 356, the equally spaced spiral cut portion 358 may have higher flexibility than the graduated spiral cut portion 356, consistent with achieving a transitional flexibility toward the distal end. As can be seen in the embodiment shown, the equally spaced spiral cut portion 358 may extend over a length of the hypotube a distance of about 1.2 in. In other embodiments however, it extends any distance within a range of about 0.5 in to 4 in. Other distances, are contemplated.

The tapered skive 350 is formed distal of the spiral portion 348 as shown in FIG. 4. The tapered skive 350 includes an connection region 364 and a tapered region 366. The connection region 364 is a region where the skive connects to the cylindrical portion of the hypotube 332. In this example, the connection region 364 comprises a curved portion having a radius that extends from the tapered region 366 to the cylindrical portion of the hypotube 332. In this example, the connection region 364 includes a round having a radius 0.02 in. However, other embodiments include rounds of other dimensions. Some embodiments include a straight taper. The tapered region 366 forms the distal portion of the hypotube 332 and its structure provides a gradual decrease in stiffness to the hypotube 332 and likewise, a gradual decrease in stiffness to the transition region 300. In the embodiment shown, the tapering skive 350 is formed as a decreasing part of a tube, where the inner and outer surfaces of the skive 350 are partially cylindrical and concentric. As can be seen in FIG. 4, the height of the skive 350, taken from a side view, decreases over the length of the skive 350. As such, because of the decreasing height, and because the skive 350 is partially cylindrical, the skive also includes a region of decreasing width when viewed from the top when the skive height is less than half the diameter of the hypotube. The tapered nature of the skive, like the graduated spiral cut, provides a continuously decreasing level of rigidity, or an increasing level of flexibility from the proximal end toward the distal end.

In one example, the skive 350 has a proximal region adjacent the connection region 364 having a height or thickness within a range of about 0.040 to 0.010 in. In one embodiment, the height or thickness is about 0.020 in. This proximal region tapers to a distal region with a distal tip having a thickness less than that of the proximal region. In one embodiment, the distal region has a height or thickness in a range of about 0.020 to 0.004 in. In one embodiment, the height or thickness is about 0.0070 in. Other sizes are contemplated. In some embodiments, the skive has a length in the range of about 1-4 in and in some embodiments, about 1.5-2.5 in. In one embodiment, the skive has a length of about 2 in. In some embodiments, the skive includes a rounded distal tip. Because the cross-sectional area of the skive decreases along the length of the skive, the flexibility of the skive increases. That results in a transition from the stiffer proximal region and a less stiff or more flexible distal region.

FIGS. 5 and 6 are cross-sectional views taken along the lines 5-5 and 6-6 in FIG. 2. As can be seen in these Figures, the cross-sectional area of the skive 350 decreases as the skive 350 extends longitudinally in the proximal direction.

Still referring to FIGS. 3, 5, and 6, the polymer jacket 334 surrounds the distal portion of the hypotube 332 and provides stability and support to the spiral cut region 348. In the embodiment, shown, the polymer jacket 334 cooperates with the spiral cut region 348 to strengthen, and in some embodiments, maintain the integrity to provide predictable flexibility of the spiral cut region 348. In addition, the polymer jacket 334 may protect tissue from becoming pinched, rubbed, or for otherwise interfacing with an edge of the spiral cut hypotube 332.

In the embodiment shown, the polymer jacket 334 extends over the spiral cut region 348 and over at least a portion the proximal region of the skive 350. In some embodiments, it extends proximally from the spiral cut region 348 to near the proximal end of the hypotube, thereby covering nearly the entire length of the hypotube 332. In other embodiments, it extends in the area of the transition region 300 only. In some embodiments, the polymer jacket 334 has a thickness in the range of about 0.005 in, and is formed of biocompatible material as is known in the art.

As can be seen in FIG. 6, the distal portion of the polymer jacket 334 envelops or encompasses the microcable 340 so that the microcable 340 is embedded in the polymer jacket 334 and is secured in place. The microcable 340 projects from the distal end of the polymer jacket to be enclosed within the outer distal shaft 336.

The outer distal shaft 336 extends from the transition region 300 to the distal end 224 of the imaging device 200. As can be seen in the cross-sectional image of FIG. 6, the outer distal shaft 336 is formed to envelop or encompass the inner member 338. It also envelops the microcable 340 when the microcable 340 extends from the polymer jacket 334.

With the microcable 340 enveloped in the polymer jacket 334 and the inner member enveloped in the outer distal shaft 336, the arrangement results in the microcable being immovably disposed directly between the skive 350 and the inner member 338.

The inner member 338 is maintained in the outer distal shaft 336. It defines a guidewire lumen that is sized to receive a guide-wire (not shown). In one embodiment, the guidewire lumen has a diameter of 0.017 in such that it can receive a 0.014 in diameter guidewire. Typically, a guide-wire is first inserted into a patient's artery. The imaging device 200 is then placed over the guide-wire such that the inner member 338 encompasses the guide-wire. In some examples, the inner member 338 may extend the entire length of the imaging device, such as in the imaging device 100. The length of the inner member 338 is long enough to extend from the point at which the catheter starts on the guide-wire (typically, the tip) to the point at which the guide-wire exits the catheter. Thus, the length may be relatively short in the case of a rapid exchange catheter and relatively long in the case of an over-the-wire catheter. The inner member has a proximal open end 370 that is disposed above the skive 350 and just distal of the end of the cylindrical portion of the hypotube 332.

As can be seen in the exemplary embodiment of FIG. 2, the outer distal shaft 336 extends over the distal end of the polymer jacket 334. This provides continuity and enables a smooth flexible transition from the stiffer proximal portion to the more flexible distal portion. In some embodiments, the outer distal shaft 336 abuts against the distal end of the polymer jacket 334 without overlap.

While it is recognized that the spiral cut 352 may by itself may provide some transition, and the skive 350 by itself may provide some additional transition, the two together may provide an increased graduated flexibility without compromising structural integrity.

FIGS. 8-11 show another embodiment of a transition region, referenced herein by the numeral 400 that may replace either of the transition regions 130, 230 on the imaging device 100, 200. This embodiment includes a hypotube 402, a polymer jacket 404, a stiffening wire 406, an outer distal shaft 408, and a microcable 410. The hypotube 402 in this embodiment is shown in FIG. 9 and includes a skive 412 extending at its distal end. In this embodiment, instead of being a tapering skive as discussed above, the skive 412 is a short and blunt skive. In some embodiments, the skive 412 extends from a distal end of a cylindrical section of the hypotube 402 a distance within a range of about 0.1 to 0.5 in.

The skive 412 includes an connection region 420 and a protruding region 422. The connection region 420 transitions the cylindrical portion of the skive 412 to the protruding region 422 and is formed of a round having a radius within a range of about 0.005 to 0.003, although other ranges and shapes are contemplated. In this case however, the relatively short distance of the protruding region 422 of the skive 402 does not provide all the desired stiffness in this embodiment. In order to provide a smooth transition from the relatively more stiff to the proximal portion 204 to relatively less stiff distal portion 206, the transition region 400 includes a stiffening element shown as the stiffening wire 406.

The protruding region 422 extends distally from the connection region 420 and is formed to have substantially the same shape and cross-section along its length. In this embodiment, the skive extends about 0.2 in from the cylindrical portion of the hypotube, although longer and shorter skives are contemplated.

In this embodiment, the stiffening wire 406 is formed of a relatively stiff material that may flex under load. For example, the stiffening wire 406 may be formed of a metal material, such as stainless steel, although other materials may be used. The stiffening wire 406 tapers from an proximal outer diameter to a distal outer diameter. The taper provides a continuous but gradual change in stiffness, as the cross-sectional area of the stiffening wire decreases in the distal direction. In some embodiments, the proximal end of the stiffening wire 406 has a diameter within a range of about 0.01 in to 0.03 in. In some of these embodiments, the range is about 0.01 to 0.02 in, and in one embodiment, is about 0.015 in. Other dimensions, both larger and smaller are contemplated. The distal end of the stiffening wire 406 has a diameter within a range of about 0.0001 to about 0.01 in, and in some embodiments about 0.0001 to about 0.001. In some embodiments, the diameter is about 0.0003 in. Other dimensions, both larger and smaller are contemplated. The proximal end of the stiffening wire 406 is disposed on the skive 412 using an adhesive, a weld, solder, or other attachment method. In one embodiment, the stiffening wire 460 is soldered to the curved inner surface of the skive 412. In one embodiment, the diameter of the stiffening wire 406 is selected to easily mate with the inner diameter of the skive 412. The stiffening wire 406 is, in the embodiment shown, between about 1-2 in long. In this embodiment, the stiffening wire 406 has a cylindrical cross-section, and therefore, may flex in any direction with an equal stiffness or deflection. Stiffening wires with other cross-sectional shaped, such as square, oval, and others are also contemplated.

The polymer jacket 404 extends over the distal end of the hypotube 382, and in one embodiment extends substantially the entire length of the hypotube 382 in the manner discussed above. In other embodiments, the polymer jacket 404 extends on the cylindrical portion of the hypotube 402 to a point just distal of the skive 412. In other embodiments, the polymer jacket 404 may extend distally the entire length of the stiffening wire 406. In one embodiment, the polymer jacket 404 extends the entire length of the distal portion 106. The microcable 410 may be embedded within the polymer jacket 404 in the manner discussed above with reference to FIG. 3. In one embodiment, the outer distal shaft 408 extends from within a distal end of the polymer jacket 404 to the distal end 224 of the imaging device 200. In some embodiments, the outer distal shaft 408 surrounds or encases the microcable 410, such that the microcable 410 is embedded within the outer distal shaft 408.

FIG. 11 shows an end view of the hypotube 402, the stiffening wire 406, and the microcable 410. As can be seen, the microcable 410 extends over the stiffening wire 406 as it extends toward the distal end 221 of the imaging device 200. In this example, the stiffening wire 406 is disposed within the skive 412 and the microcable 410 is disposed to pass directly over the stiffening wire 406. In some embodiments, the microcable 410 and the stiffening wire are embedded within the polymer jacket 404 in the manner shown in FIG. 7 above, such that they are fixed in place relative to each other in the transition region 400.

Although not shown in FIG. 8, some embodiments include an inner member sized and arranged to receive a guidewire in the manner discussed above relative to FIG. 3. In such embodiments, the inner member may have a proximal opening disposed adjacent the skive 412, and an associated guidewire may extend out of the inner member and be disposed adjacent the proximal portion of the hypotube as the imaging device is introduced into the patient's vasculature.

The stiffening wire 386 provides a continuous, smooth, and gradual transition from the more stiff hypotube to the less stiff distal portion 306, reducing the likelihood of kinks and providing an easy to advance system. In addition, because the stiffening is symmetrically formed, the transition region has a substantially similar flexibility in all directions.

FIGS. 12-15 show another embodiment of a transition region 450 that may form the transition region 130 or 230 on the imaging devices 100, 200. This embodiment includes a hypotube 452, the polymer jacket 404, the stiffening wire 406, the outer distal shaft 408, and the microcable 410. Accordingly, a difference between the transition region 400 and the transition region 450 is the hypotube 452, with the remaining elements being similar to those discussed above. Accordingly, their description is not repeated here.

Figure 15:
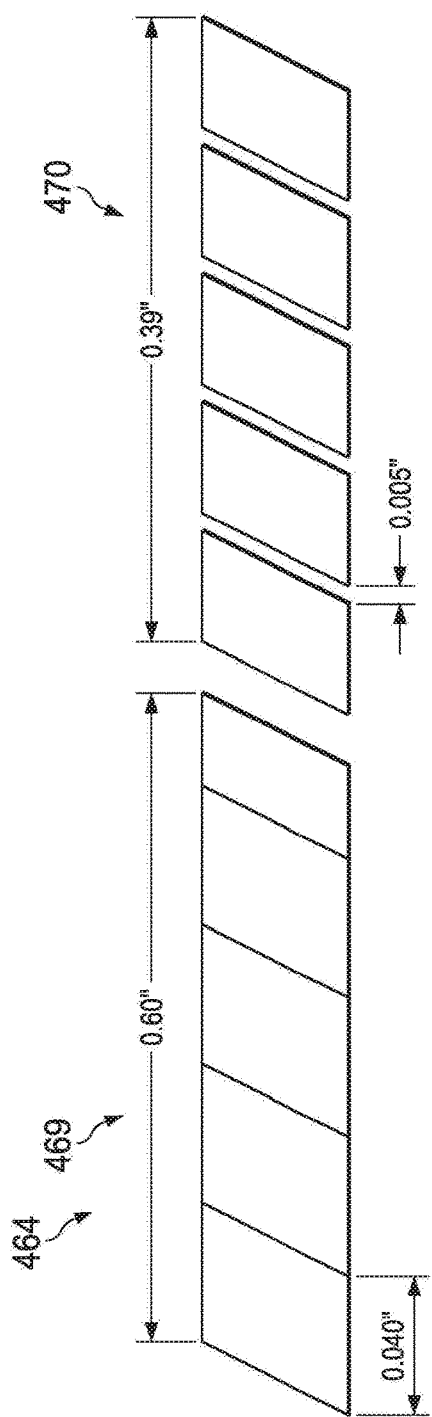
FIG. 15 illustrates a side view of a portion of an exemplary hypotube of the transition region of FIG. 12 according to an exemplary aspect of the present disclosure.
Figure 16:
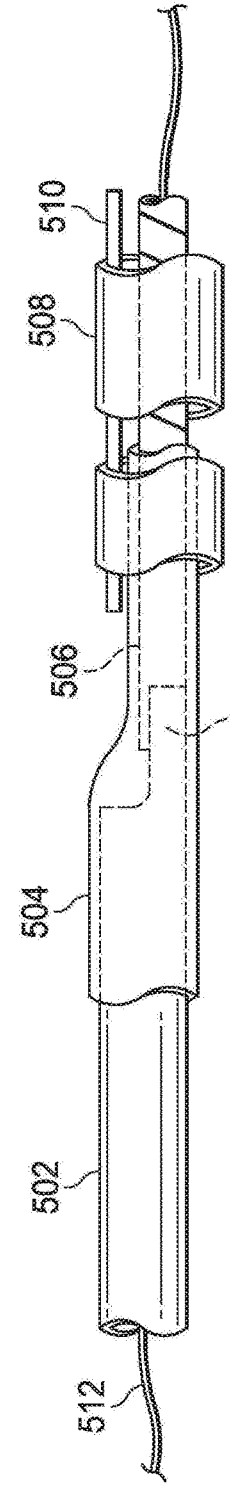
FIG. 16 illustrates a side view of a transition region of an imaging device according to an exemplary aspect of the present disclosure.

In this embodiment, the hypotube 452 is similar in structure to the hypotube 402 discussed above, but includes a cut region 464 with a cut 466 formed therein to reduce the stiffness of the hypotube 152 at its distal end adjacent its skive 468. In this embodiment, the cut 466 is a tapered cut and extends from a location adjacent the skive 468 in the proximal direction. In some embodiments, the cut 466 is a tapered cut extending about the exterior of the hypotube 452. FIG. 15 shows spacing of the cut 466 according to one exemplary embodiment. In the embodiment in FIG. 15, the cut region 464 includes a standard spiral cut region 469 and a spaced spiral cut region 470. In the standard spiral cut region 469, the cut 466 is thin so that the adjacent surfaces of the segments between cuts are abutting or nearly abutting. In the example in FIG. 15, the segments have a length of about 0.040 in. The discussion above relating to cuts, including the various lengths of cuts, also applies to the cuts in FIGS. 12-15. The spaced spiral cut region 470 is a wide cut to create a space between adjacent segments. In this embodiment, the spacing is 0.005 in between adjacent segments. This cut spacing adds additional flexibility to the spaced spiral cut region 470. Accordingly, while the standard spiral cut region 469 is more flexible than the cylindrical portion of the hypotube 452, the spaced spiral cut region 470 is even more flexible than the standard spiral cut region 469.

In the embodiment shown, the spiral cut region 464 extends about an 1.5 in. However, other lengths are contemplated. In addition, any of the dimensions disclosed herein may be adjusted to find an optimum value. Furthermore, in some embodiments, the cut 466 is graduated as discussed above.

FIGS. 16-20 show another embodiment of a transition region 500 that may form the transition region 130 or 230 on the imaging devices 100, 200. This embodiment includes a hypotube 502, a polymer jacket 504, a stiffening element shown as a midsection hypotube 506, an outer distal shaft 508, an inner member 510, and a microcable 512. The hypotube 502 may be similar to the hypotube 402 and includes a skive 516.

The stiffening element or midsection hypotube 506 may be attached to the skive 512 in the manner discussed above relative to the stiffening wire 406. The midsection hypotube 506 in this embodiment is a cylindrical tube having a proximal cylindrical portion 520 and a distal cylindrical portion 522, with the distal cylindrical portion 522 having a spiral cut 524. The spiral cut 524 yields more flexibility at the distal cylindrical portion 522 than the proximal cylindrical portion 524 end as discussed above. In this embodiment, the midsection hypotube 506 has length in the range of about 4-16 in. In some embodiments, the length is about 6-10 in, and in one embodiment, the midsection hypotube 506 has a length of about 8 in. Other lengths are contemplated. The distal cylindrical portion 522 with the spiral cut 524 may have a length of about 0.5-6 in, and in some embodiments, may form about a quarter of the total length of the midsection hypotube 506. Other lengths are contemplated. In some embodiments, the distal cylindrical portion 522 may have a length of about 1-3 in, and in one embodiment, about 2 in. The spiral cut 524 may form a plurality of segments that may have a length about 0.020 in, although other lengths are contemplated. Some embodiments have spiral cut spacing or gaps in the manner discussed above relative to the hypotube 332 or the other hypotubes discussed herein. The midsection hypotube 506 may be sized for insertion into and connection to the hypotube and in some embodiments, has an inner diameter of about 0.013 in and an outer diameter of about 0.016 in. Other sizes are contemplated. Because the midsection hypotube 506 has a hollow center, the microcable 512 extends through the midsection hypotube 506 in the manner shown in FIGS. 17 and 20.

Figure 17:
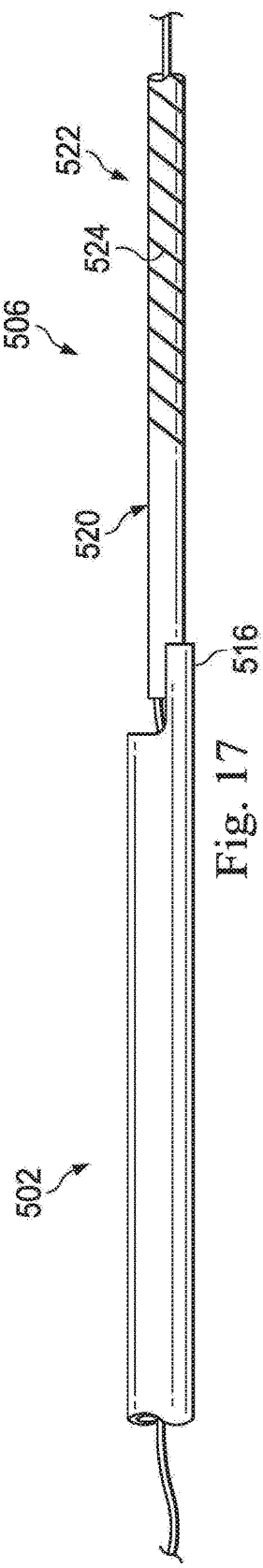
FIG. 17 illustrates a side view of selected elements of the transition region of FIG. 16 according to an exemplary aspect of the present disclosure.
Figure 20:
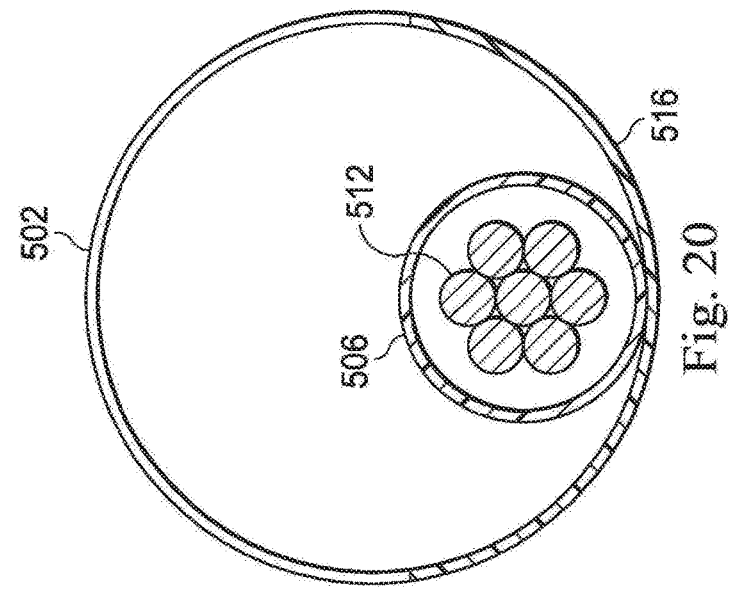
FIG. 20 illustrates an end view of selected elements of the transition region of FIG. 16 according to an exemplary aspect of the present disclosure.
Figure 18:
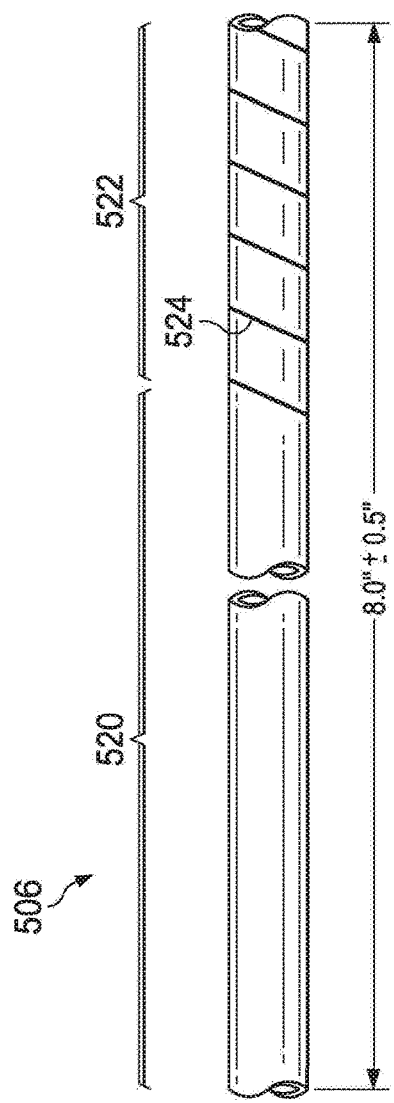
FIG. 18 illustrates a side view of a portion of an exemplary stiffening element of the transition region of FIG. 16 according to an exemplary aspect of the present disclosure.
Figure 19:
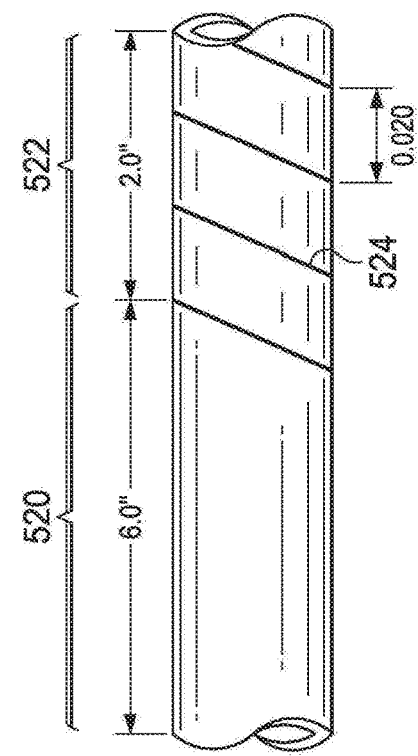
FIG. 19 illustrates a side view of a portion of an exemplary stiffening element of the transition region of FIG. 16 according to an exemplary aspect of the present disclosure.

FIG. 20 is an end view of the components in FIG. 17. As can be seen, because the midsection hypotube 506 is attached to the skive 516, the midsection hypotube is disposed low in the hypotube 502.

The polymer jacket 504 extends as discussed with reference to other embodiments disclosed herein, and encases the distal end of the midsection hypotube 506. In this embodiment, a distal portion of the polymer jacket 504 extends into the outer distal shaft 508. However, as discussed above, the polymer jacket 504 and the outer distal shaft 508 may abut at ends. In some embodiments, the polymer jacket 504 extends along the length of the midsection hypotube 506 and covers the distal cylindrical portion 522 of the midsection hypotube 506, having the spiral cut 524.

The inner member 510 is disposed as discussed with reference to other embodiments disclosed herein, and includes a proximal opening that is aligned with the midsection hypotube 506, and in some embodiments, is adjacent the skive 516, and may be directly above the skive 516. In some embodiments, the inner member is encased in the outer shaft as discussed above relative to FIG. 7. In such embodiments, the inner member may be encompassed and located directly above the midsection hypotube 506 and the microcable 512 so that the microcable is disposed directly between the skive 516 and the inner member. In alternative embodiments, the imaging device is an over-the-wire device and the inner member does not have a proximal opening within the transition region 500, but instead the opening is at the proximal portion of the elongate flexible body or elsewhere.

The transition region 500 includes a cylindrical hypotube portion having a first stiffness, a midsection hypotube 506 having a proximal cylindrical portion 520 with a second stiffness less than the first stiffness and having a distal cylindrical portion 522 with a spiral cut having a third stiffness less than the second stiffness, and an outer distal shaft 508 having a fourth stiffness less than the third stiffness. Thus, the transition region provides a gradual transition in stiffness from the proximal portion 204 of the imaging device 200 to the distal portion 206.

Figure 21:
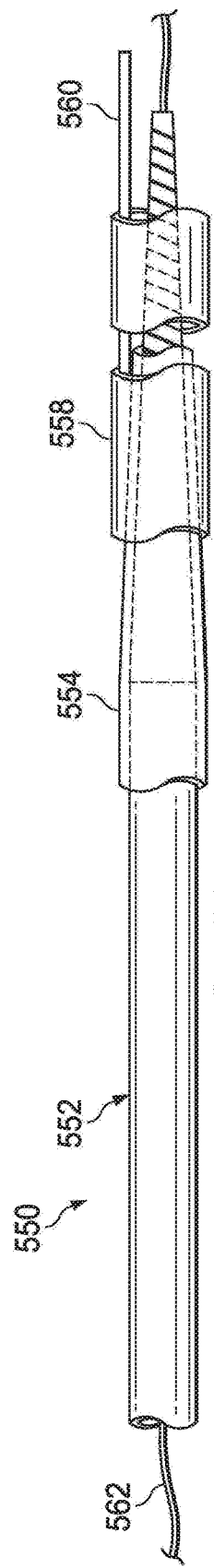
FIG. 21 illustrates a side view of a transition region of an imaging device according to an exemplary aspect of the present disclosure.
Figure 22:
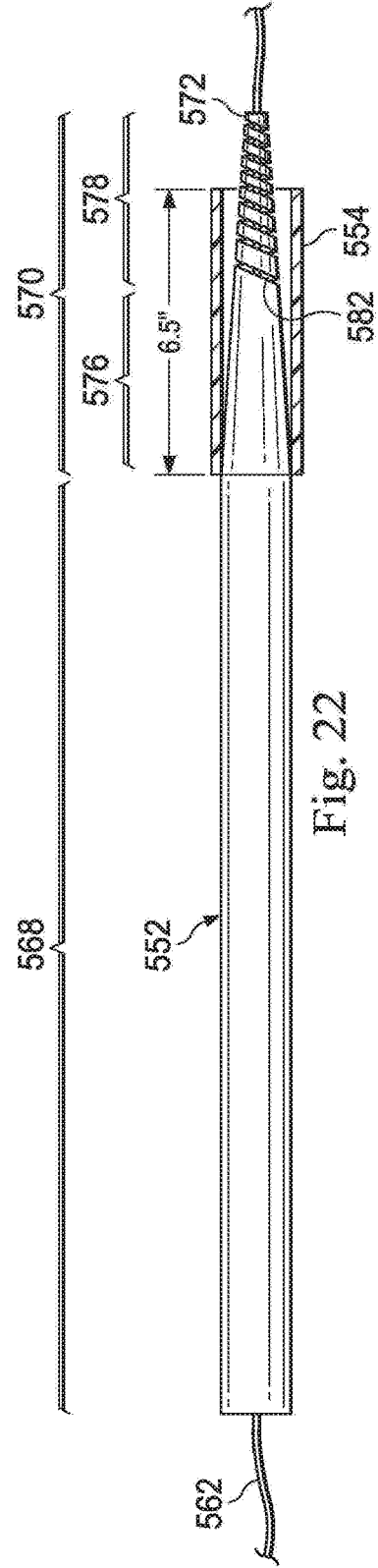
FIG. 22 illustrates a side view of selected elements of the transition region of FIG. 16 according to an exemplary aspect of the present disclosure.

FIGS. 21 and 22 show an alternative embodiment of a transition region 550 that may form the transition regions 130, 230 in the imaging devices 100 and 200. The transition region 550 includes a hypotube 552, a polymer jacket 554, an outer distal shaft 558, an inner member 560, and a microcable 562.

FIG. 21, like many of the figures discussed above, shows different elements of the transition region 550 in partial transparent view to show the exemplary relationship between the different elements. FIG. 22 shows the hypotube 552, the polymer jacket 554 as a partially transparent image disposed over the hypotube 552, and the microcable 562.

Referring to FIG. 22, the hypotube in this embodiment includes a cylindrical portion 568 and a tapering distal end 570. The cylindrical portion 568 may be as discussed above. The tapering distal end 570 in this embodiment has a frustum or a conical end taper extending from the diameter of the cylindrical portion 568 to a narrow distal tip 572. In this embodiment, the tapering distal end 570 has a length within a range of about 4-12 in, and in some embodiments, a length of about 7-9 in. Other lengths however are contemplated. In this embodiment, the tapering distal end 570 includes a solid tapering region 576 and a spiral cut region 578. While shown as having substantially equal lengths in the exemplary embodiment in FIG. 22, other lengths are contemplated. For example, the spiral cut region 578 may form all or part of the tapering distal end 570. Likewise, the solid tapering region 576 may form all or part of the tapering distal end 570. In some examples, the spiral cut region 578 extends about 25% of the length of the tapering distal end 570. In this embodiment, when the tapering distal end 570 is about 8 in, the spiral cut region may be about 2 in. Furthermore, in order to provide a transition from the stiffer proximal portion 204 of the imaging device 200 to the more flexible distal portion 206, the hypotube 552 may have an outer diameter at its cylindrical portion of about 0.0230, and the spiral cut may start on the conical tapering distal end 570 at a diameter of about 0.0135 in, and may taper toward the distal tip 572. In some embodiment, the narrow distal tip has a hole therethrough having a diameter or width of about 0.0160 in.

In the exemplary embodiment shown, the spiral cut region 578 includes a spiral cut 582 that divides the spiral cut region 578 into segments as discussed above. As can be seen, the segments are graduated in the manner discussed above. Furthermore, the spiral cut 582 in the embodiment shown is a spaced spiral cut. Accordingly, the discussion above applies equally to the transition region 550 in FIGS. 21 and 22. In some embodiments however, the spiral cut is not spaced, but the edges of adjacent segments are disposed against or abut against one another.

The polymer jacket 554 is shown in FIG. 22 as a cylindrical portion extending over at least a portion of the tapering distal end 570. However, as discussed above, some embodiments include a polymer jacket 554 that extends along substantially the entire length of the hypotube. Further, when assembled, the polymer jacket 554 is shrunk to form-fit around the profile of the hypotube. This can be better seen in FIG. 21, where the polymer jacket 554 tapers with the tapering distal end 570. In some embodiments, the polymer jacket 554 extends to the distal tip 572, thereby covering the spiral cut 582.

In this embodiment, the outer distal shaft 558 also extends over a portion of the tapering distal end 570. In the exemplary embodiment shown, the outer distal shaft covers the spiral cut region 578.

Because of the diametrical decrease due to the conically tapering shape of the tapering distal end 570, the inner member 560 extends along a portion of the tapering distal end 570, but its proximal opening is disposed distal of the proximal end of tapering distal end 570. Accordingly, a guidewire in the inner member 560 may extend out of the proximal opening of the inner member and along a portion of the tapering distal end 570.

In the example shown, the microcable 562 extends through the center of the hypotube and out of the distal tip 572. Accordingly, the microcable 562 is disposed centrally in the elongated member in at least a portion of the transition region 550, and the inner member 558 is disposed along an outer edge of the outer shaft. As discussed above, the inner member 558 and the microcable may be encased or embedded within the inner member 560 and the polymer jacket 554.

It should be noted that reference to a spiral cut may also include multiple spiral cuts. It should also be noted that due to similarities in components between the disclosed transition regions, any of the description provided with respect to one embodiment may equally apply to any other embodiment.

An illustrative method for fabricating an imaging device according to an exemplary aspect of the present disclosure includes shaping a distal end of a hypotube to conform to the any of the embodiments disclosed herein. Accordingly, shaping a distal end of a hypotube may include cutting, snipping, grinding or otherwise forming a skive on the hypotube or forming a taper on the hypotube. In some embodiments, the next step is changing the flexibility of the hypotube by forming a cut in the hypotube. This may be done, for example, by laser cutting or other methods known in the art. In some embodiments, the cut is a single taper cut around the circumference of the hypotube, while in other embodiments, the cut is a plurality of tapering cuts around the circumference of the hypotube. With the cuts formed, the microcable may be fed through the hypotube and out the distal end. A polymer jacket may then be formed around the hypotube. This may be done through any form known in the art, including applying a sleeve, applying a spray, dipping the hypotube, and other methods. In some embodiments, the polymer jacket encases a portion of the microcable to prevent its further movement at a particular location, such as where the inner member and the microcable overlap. In some embodiments, the polymer jacket covers a part or all of the skive. The distal portion may then be attached by introducing the distal end of the hypotube, along with the microcable, into the outer distal shaft. In some embodiments, the outer distal shaft is pre-formed with the inner member disposed therein. In other embodiments, the outer distal shaft and the inner member and the distal end of the hypotube are all connected simultaneously. In some embodiments, the outer distal shaft extends over a part of the polymer jacket. This may reduce the chance of distal and proximal portions separating during use. The outer distal shaft is then welded, melted, or otherwise attached to the hypotube. In some embodiments, in order to accommodate the microcable, the inner shaft is disposed to be directly opposite the skive or other member so that the microcable is disposed directly between the inner member and the skive or the other supporting member. In some embodiments, the method includes brazing, welding, or otherwise adhering a wire or midsection tube to the hypotube. This also may include generating cuts or otherwise affecting the flexibility of the wire or midsection tube. With these in place, the outer distal shaft may be adhered to the polymer jacket or the hypotube in a manner that fully embeds the inner member in place.

The transition regions disclosed herein provide a transition from the proximal portion to the distal portion, increasing the robustness and decreasing potential stress risers, resulting in a more predictable device.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intraluminal device, comprising:
   a flexible elongate member configured to be positioned within anatomy of a patient, the flexible elongate member comprising a proximal portion and a distal portion, the proximal portion comprising a relatively higher stiffness and the distal portion comprising a relatively lower stiffness;
   a transition region disposed between the proximal portion and the distal portion, the transition region comprising a graduated stiffness transitioning from the stiffness of the proximal portion to the stiffness of the distal portion, the transition region comprising:
      a hypotube comprising:
         a lumen; and
         a skive at a distal portion of the hypotube, the skive comprising a tapered portion that is relatively more stiff at a proximal region and less stiff at a distal region; and
      a cable extending from the proximal portion of the flexible elongate member over the skive to a functional element, wherein the cable is disposed within the lumen of the hypotube; and
      a polymer jacket extending over at least a portion of the hypotube and the skive, wherein the polymer jacket comprises an inner surface surrounding a lumen, and wherein the tapered portion of the skive and a portion of the cable are positioned within the lumen of the polymer jacket such that the tapered portion of the skive and the cable are fixed in place relative to one another by the inner surface of the polymer jacket and an inner surface of the tapered portion of the skive.

2. The intraluminal device of claim 1, wherein the polymer jacket comprises a circular cross section at a proximal region of the polymer jacket, and a non-circular cross section at a skive region distal of the proximal region, wherein the inner surface of the polymer jacket is disposed at the skive region of the polymer jacket.

3. The intraluminal device of claim 1, further comprising:
an outer distal shaft extending over the distal region of the skive and a distal portion of the polymer jacket; and
an inner member embedded within the outer distal shaft and configured to receive a guidewire, wherein the cable is disposed between the skive and the inner member.

4. The intraluminal device of claim 3, wherein the inner member has an opening end in the transition region.

5. The intraluminal device of claim 3, wherein the cable lies within the skive.

6. The intraluminal device of claim 1, comprising an outer distal shaft portion forming a part of the transition region, the outer distal shaft portion extending over the distal region of the skive to provide a graduated flexibility transition from the skive to the distal portion.

7. The intraluminal device of claim 1, wherein the skive has a length within a range of about 1-4 inches.

8. The intraluminal device of claim 1, wherein the hypotube includes a cylindrical portion proximal of the skive and a connection region proximal of the tapered portion, wherein the tapered portion comprises a curved edge to meet the cylindrical portion.

9. The intraluminal device of claim 1, wherein the hypotube further comprises a spiral cut proximal of the skive, the spiral cut decreasing the stiffness of the hypotube.

10. The intraluminal device of claim 9, wherein the hypotube includes a cylindrical portion proximal of the skive, the spiral cut being formed on the cylindrical portion.

11. The intraluminal device of claim 9, wherein the hypotube comprises a single structure.

12. The intraluminal device of claim 9, wherein the hypotube is formed of separate structures.

13. The intraluminal device of claim 9, wherein the polymer jacket extends over the spiral cut.

14. The intraluminal device of claim 13, further comprising an outer distal shaft portion forming a part of the transition region, the outer distal shaft portion extending over a portion of the skive and over a distal portion of the polymer jacket to provide a stiffness transition.

15. The intraluminal device of claim 14, wherein the spiral cut is graduated such that the spiral cut creates segments having a longitudinal length greater in a proximal direction and shorter in a distal direction.

16. The intraluminal device of claim 1, wherein the tapered portion comprises a skive proximal region and a skive distal region, the skive proximal region having a first cross-sectional area and the skive distal region having second cross-sectional area, the first cross-sectional area being larger than the second cross-sectional area such that the skive proximal region has a greater stiffness than the skive distal region.

17. The intraluminal device of claim 1, wherein the functional element is an imaging element.

* * * * *